United States Patent [19]

Ashikari et al.

[11] Patent Number: 4,863,864
[45] Date of Patent: Sep. 5, 1989

[54] GLUCOAMYLASE GENE OF RHIZOPUS ORYZAE

[75] Inventors: Toshihiko Ashikari; Norihisa Nakamura; Yoshikazu Tanaka; Yuji Shibano; Hajime Yoshizumi, all of Osaka, Japan

[73] Assignee: Suntory Limited, Osaka, Japan

[21] Appl. No.: 808,742

[22] Filed: Dec. 13, 1985

[30] Foreign Application Priority Data

Dec. 15, 1984 [JP] Japan ................... 59-264964

[51] Int. Cl.[4] .............. C12N 9/34; C12N 15/00; C12N 1/18; C07H 15/12
[52] U.S. Cl. .................... 435/205; 435/91; 435/172.3; 435/255; 435/320; 435/942; 536/27; 935/18; 935/19; 935/28; 935/37; 935/41; 935/60; 935/69
[58] Field of Search ............ 435/172.3, 253, 91, 435/254, 255, 320, 68, 942, 205; 536/27; 935/18, 19, 28, 37, 41, 60, 69

[56] References Cited

U.S. PATENT DOCUMENTS 4,469,791 9/1984 Colson et al. ............... 435/253

FOREIGN PATENT DOCUMENTS 0126206 11/1984 European Pat. Off. .

OTHER PUBLICATIONS

Valenzuela, P. et al., Nature vol. 298, pp. 347–350 (1982).
Maniatis et al., Moleculer Cloning, a Laboratory Manual CSH Laboratory (1982).
Boel et al., "Glucoamylases G1 and G2 from *Aspergillus Niger* are Synthesized from two Different but Closely Related mRNA's", *EMBO J.*, vol. 3, No. 5 (1984) pp. 1097–1102.
J. Biochem. vol. 92, No. 5, 1982, pp. 1623–1633.
Agric. Biol. Chem., 50(4), 965–969, 1986.
"Idenshi-Kokagaku (Genetic Engineering)", Ch. 12 (1987), ed. Tadahiko Ando and Kenji Sakaguchi, Pub. by Kyoritsu Shuppan Ko. Ltd.

*Primary Examiner*—Elizabeth C. Weimar
*Assistant Examiner*—Joan Ellis
*Attorney, Agent, or Firm*—Cushman, Darby & Cushman

[57] ABSTRACT

The present invention relates to the Rhizopus derived glucoamylase gene, a novel recombinant vector comprising said gene, and a microorganism transformed by said vector, as well as a process for reproducing Rhizopus glucoamylase by cultivating the transformed microorganism, especially yeast, in a liquid medium.

12 Claims, 19 Drawing Sheets

Fig. 1(a)

```
GATCTCAATT TGTGTTGTGA TATATTCAGA TTTAAAATTT CAAACATATA TAAGACGCGT TTATTTCCTC GTTTTTCAAA AATCATCACT
                                                                60

TGTCTTCAAA TTGATCTTTC TCTA ATG CAA CTG TTC AAT TTG CCA TTG AAA GTT TCA TTC TTT CTC GTC CTC TCT TAC
               MET GLN LEU PHE ASN LEU PRO LEU LYS VAL SER PHE PHE LEU VAL LEU SER TYR
               120                                                               240

TTT TCT TTG CTC GTT TCT GCT GCA AGC ATT CCT AGT AGT GCT TCT GTC CAG CTT GAT TCA TAC AAT TAC GAT
PHE SER LEU VAL SER ALA ALA SER ILE PRO SER SER ALA SER VAL GLN LEU ASP SER TYR ASN TYR ASP
    180                                                                    300

GGC TCT ACT TTT TCA GGA AAA ATT TAT GTC AAG AAC ATT GCT TAC TCC AAG AAG GTT ACT GTA ATT TAC GCC
GLY SER THR PHE SER GLY LYS ILE TYR VAL LYS ASN ILE ALA TYR SER LYS LYS VAL THR VAL ILE TYR ALA

GAT GGC TCT GAC AAC TGG AAT AAT GGA AAC ACC ATT GCT GCT TCT TAC TCT GCT CCT ATT TCT GGA TCA
ASP GLY SER ASP ASN TRP ASN ASN GLY ASN THR ILE ALA ALA SER TYR SER ALA PRO ILE SER GLY SER
                                            360                                        420

AAT TAC GAA TAC TGG ACA TTC TCT GCC TCC ATT AAT GGT ATC AAG GAG TTC TAC ATT AAG TAT GAG GTC AGT
ASN TYR GLU TYR TRP THR PHE SER ALA SER ILE ASN GLY ILE LYS GLU PHE TYR ILE LYS TYR GLU VAL SER

GGA AAA ACA TAT GAT AAC AAC AAT TCT GCC AAT TAC CAA GTA TCT ACA TCC AAG CCT ACT ACT ACT ACT
GLY LYS THR TYR ASP ASN ASN ASN SER ALA ASN TYR GLN VAL SER THR SER LYS PRO THR THR THR THR
                              480                                                  600

GCT ACT GCT ACT ACT ACC GCT CCT TCC ACT ACG ACT ACC ACT TCA AGC TCT GAG CCA GCT ACT
ALA THR ALA THR THR THR ALA PRO SER THR THR THR THR THR SER SER SER GLU PRO ALA THR
                    540                                                    660

TTC CCA ACT AAC GGT ATC TCC ACA ATC TCC TCA TGG ATT AAG AAG CAA GAA GGT ATC GGC TTT GCT ATG CTT
PHE PRO THR ASN GLY ILE SER THR ILE SER SER TRP ILE LYS LYS GLN GLU GLY ILE GLY ILE SER ARG PHE ALA MET LEU
```

Fig. 1(b)

```
CGA AAC ATC AAT CCT GGA AGC GCT ACC TTC ATT GCT GCC TCA CTC TCT ACC GCT GGT CCC GAT TAC
Arg Asn Ile Asn Pro Gly Ser Ala Thr Phe Ile Ala Ala Ser Leu Ser Thr Ala Gly Pro Asp Tyr
                                                    720

TAC TAT GCT ACT TGG ACT CGT GAT GCT GCA TTA ACC TCC AAT GTA ATT GTT TAC GAA TAC AAC ACT ACT TTG TCC
Tyr Tyr Ala Thr Trp Thr Arg Asp Ala Ala Leu Thr Ser Asn Val Ile Val Tyr Glu Tyr Asn Thr Thr Leu Ser
                                780

GGT AAT AAG ACT ATC CTC AAC GTC CTC AAG GAC TAT GTT ACA TTC TCA GTC AAG ACC CAA TCA ACT TCT ACC
Gly Asn Lys Thr Ile Leu Asn Val Leu Lys Asp Tyr Val Thr Phe Ser Val Lys Thr Gln Ser Thr Ser Thr
                840

GTC TGT AAC TGC CTT GGT GAG GGT CTT AAT CCT GAG CCT TTC TCT GGT TAT ACT GGT GCT TGG GGA AGA CCT
Val Cys Asn Cys Leu Gly Glu Gly Leu Asn Pro Asp Pro Phe Ser Gly Tyr Thr Gly Ala Trp Gly Arg Pro
        900                                                                                         960

CAA AAT GAT GGA CCT GCT GAA CGT ACT CTC ATT TTG TTT GCT GAC AGT TAT CTT TAT ACT CAA ACA AAG
Gln Asn Asp Gly Pro Ala Glu Arg Thr Leu Ile Phe Leu Phe Ala Asp Ser Tyr Leu Tyr Thr Gln Thr Lys
                                                1080

GAT GCT TCC TAT GTC ACT GGT ACA CTC AAG CCT GCT ATC TTC AAG GAC TTG GAC TAT GTC GTC AAT GTC TGG
Asp Ala Ser Tyr Val Thr Gly Thr Leu Lys Pro Ala Ile Phe Lys Asp Leu Asp Tyr Val Val Asn Val Trp
                        1080

TCT AAT GGC TGT TTC GAT TTA TGG GAA GAA GTC AAC GGT GTT CAC TTC TAT ACT TAT ACT TTA ATG GTT CGT AAG
Ser Asn Gly Cys Phe Asp Leu Trp Glu Glu Val Asn Gly Val His Phe Tyr Thr Leu Met Val Arg Lys
                                1140

GGT TTG CTT CTT GGT GCA GAT TTC GCT GCA AAA CGT AAC CGT GCA TCT GAC TCT ACC TAT AGC AGC ACT
Gly Leu Leu Leu Gly Ala Asp Phe Ala Lys Arg Asn Arg Ala Ser Asp Ser Thr Tyr Ser Ser Thr
                        1200                                                                        1320

GCA TCC ACT ATT GCA AAC AAG ATC TCT TCT AAT AAC TGG ATT CAA GTC AGT CAA AGC
Ala Ser Thr Ile Ala Asn Lys Ile Ser Ser Asn Asn Trp Ile Gln Val Ser Gln Ser
    1260
```

Fig. 1(c)

```
GTT ACT GGT GTC AGT AAA AAG GGT TTG GAT GTC TCC ACA TTG GCT GCT AAC CTT GGT AGT GTT GAT
Val Thr Gly Val Ser Lys Lys Gly Leu Asp Val Ser Thr Leu Ala Ala Asn Leu Gly Ser Val Asp
                                                                   1380
                                                       1440
GAT GGA TTC TTC ACT CCT GGC TCT GAA AAG ATC CTT GCC ACT GCT GTT GAA GAC TCC TTC GCT TCC
Asp Gly Phe Phe Thr Pro Gly Ser Glu Lys Ile Leu Ala Thr Ala Val Glu Asp Ser Phe Ala Ser
                                1500
TTG TAT CCT ATC AAC AAA CTT CCA TCT TAC CTT GGT AAC TCT ATT GGT AGA TAT CCT GAA GAC TAC
Leu Tyr Pro Ile Asn Lys Leu Pro Ser Tyr Leu Gly Asn Ser Ile Gly Arg Tyr Pro Glu Asp Tyr
                    1560
AAT GGT AAC GGA AAC TCT CAA GGA AAC TCT TTG GCT GTA ACT GGT TAC GCT GAG CTC TAT TAC CGT
Asn Gly Asn Gly Asn Ser Gln Gly Asn Ser Leu Ala Val Thr Gly Tyr Ala Glu Leu Tyr Tyr Arg
        1620                                                                       1680
GCC ATC AAG GAA TGG ATC GGT ATT GGT AAC GGT GTC ACT AGC ATA AGT TTA CCC TTC TTC AAG TTT
Ala Ile Lys Glu Trp Ile Gly Ile Gly Asn Gly Val Thr Ser Ile Ser Leu Pro Phe Phe Lys Phe
                                                                   1740
GAT TCA GCT TCT ACA TCT GGA AAG TAC ACT GTT TAC TCC GAC TTT AAC AAC CTT GCT CAA AAT ATT
Asp Ser Ala Ser Thr Ser Gly Lys Tyr Thr Val Tyr Ser Asp Phe Asn Asn Leu Ala Gln Asn Ile
GCA CTC GCT GCT GAC CGT TTG TCC TTC ACT GTC CAG CTC CAT GCT CAC CTT CAT GGT TCT CTT GAA GAG
Ala Leu Ala Ala Asp Arg Leu Ser Phe Thr Val Gln Leu His Ala His Asn Gly Ser Leu Ala Glu Glu
                                                   1800
                           1860
TTT GAC CGC ACC ACT GGT TTA TCC ACC GGT GCT AGA GAC TTG ACC TGG TCT CAC GCT TCT TTA ATC ACC GCT
Phe Asp Arg Thr Thr Gly Leu Ser Thr Gly Ala Arg Asp Leu Thr Trp Ser His Ala Ser Leu Ile Thr Ala
                               1920
TCT TAC GCT AAG GCT GGT GCA CCT GCC GCT TAAGCTGTAA ATTTAAATGC AAAGCATTAC AGCTTATTTT CTTTTTCAAA
Ser Tyr Ala Lys Ala Gly Ala Pro Ala Ala

TAAAAACATA TTGATATGTT CATAACAAAA AAAAAAAAAA
```

Fig. 2(a)

```
         10          20          30          40          50          60          70          80          90
GATCTCAATT TGTGTTGTGA TATATTCAGA TTTAAAATTT CAAACATATA TAAGACGCGT TTATTCCCTC GTTTTTCAAA AATCATCACT 100         110
TGTCTTCAAA TTGATCTTTC TCTA ATG CAA CTG TTC AAT TTG CCA TTG AAA GTT TCA TTC TTT CTC GTC CTC TCT TAG
                          MET GLN LEU PHE ASN LEU PRO LEU LYS VAL SER PHE PHE LEU VAL LEU SER TYR 180                                    210                                        240
TTT TCT TTG CTC GTT TCT GCT GCA AGC ATT CCT AGT AGT GCT TCT GTC CAG CTT GAT TCA TAT AAT TAC GAT
PHE SER LEU VAL SER ALA Ala Ser Ile Pro Ser Ser Ala Ser Val Gln Leu Asp Ser Tyr Asn Tyr Asp 297             317
GGC TCT ACT TTT TCA GGA AAA ATT TAT gtaggttgca tataattcaa acattaaaaa aatattaatg ttcatgctgt acgctgt
Gly Ser Thr Phe Ser Gly Lys Ile Tyr                              INTRON 341                                            371
ag GTC AAG AAC ATT GCT TAC TCC AAG AAG GTT ACT GTA ATT TAC GCC GAT GGC TCT GAC AAC TGG AAT AAT AAT
   Val Lys Asn Ile Ala Tyr Ser Lys Lys Val Thr Val Ile Tyr Ala Asn Gly Ser Asp Asn Trp Asn Asn Asn 401                                       431                                         461
GGA AAC ACC ATT GCT TCT TAC TCT CCT ATT TCT GGA TCA AAT TAC GAA TAC TGG ACA TTC TCT GCC
Gly Asn Thr Ile Ala Ser Tyr Ser Pro Ile Ser Gly Ser Asn Tyr Glu Tyr Trp Thr Phe Ser Ala 491                                        523                              543
TCC ATT AAT GGT ATC AAG GAG TTC TAC ATT AAG gtaactttat tttactttat gatatttgcc cttatactta attaactaac
Ser Ile Asn Gly Ile Lys Glu Phe Tyr Ile Lys                                                 INTRON 563                  581                                            611
cctttttct ctatag TAT GAG GTC AGT GGA AAA ACA TAC TAT GAT AAC AAC AAT TCT GCC AAT TAC CAA Ggt aaag
                 Tyr Glu Val Ser Gly Lys Thr Tyr Tyr Asp Asn Asn Asn Ser Ala Asn Tyr Gln Val 636                                       656                      680                           710
ataata atatacaaat gcctacaact attcacattt ttatagTA TCT ACA TCC AAG CCT ACT ACT ACT GCT ACT GCT
       INTRON                                    Ser Thr Ser Lys Pro Thr Thr Thr Ala Thr Ala
```

Fig.2(b)

```
                                              740                            770
ACT ACT ACC CCT TCC ACT TCA ACC ACG ACT CCC CCA TCA AGC TCT GAG CCA ACT GCT ACT TTC CCA ACT
Thr Thr Thr Ala Pro Ser Thr Ser Thr Thr Pro Pro Ser Ser Ser Glu Pro Thr Ala Thr Phe Pro Thr
                    800                            830
GGT AAC TCT ACA ATC TCC TCA TGG TCA ATT AAG CAA GAA GGT AAG ATC AGC CGC TTT GCT ATG CTT CGA AAC ATC
Gly Asn Ser Thr Ile Ser Ser Trp Ser Ile Lys Gln Glu Gly Lys Ile Ser Arg Phe Ala Met Leu Arg Asn Ile
        860                            890                                        920
AAT CCT GGA AGC GCT ACC GGT TTC ATT GCT GCC TCA CTC TCT ACC GGT CCC GAT TAC TAC TAT GCT
Asn Pro Gly Ser Ala Thr Gly Phe Ile Ala Ala Ser Leu Ser Thr Gly Pro Asp Tyr Tyr Tyr Ala
                                              950                            980
TGG ACT CGT GAT GCT GCA TTA ACC TCC AAT GTA ATT TAC GTT GTT TAC ACT ACT TTG TCC GGT AAT AAG
Trp Thr Arg Asp Ala Ala Leu Thr Ser Asn Val Ile Tyr Val Val Tyr Thr Thr Leu Ser Gly Asn Lys
            1010                            1040                                       1070
ACT ATC AAC GTC CTC AAG GAC GTC CTG ACA TTC TCA GTC TTC TCA ACT ACT TCT ACC GTC TGT AAC
Thr Ile Asn Val Leu Lys Asp Val Leu Thr Phe Ser Val Phe Ser Thr Thr Ser Thr Val Cys Asn
                                        1100                            1130
TGC CTT GGT GAG GGT AAG TTC AAT CCT GAT GGT TCT GGT TAT AGT TAT ACT CTT ACT CAA ACA CCT CAA AAT GAT
Cys Leu Gly Glu Gly Lys Phe Asn Pro Asp Gly Ser Gly Tyr Ser Tyr Thr Leu Thr Gln Thr Pro Gln Asn Asp
                                              1190
GGA CCT GCT GAA CGT GCT ACT ACC TTC ATT TTG TTT GCT GAC AGT TAT CTT ACT CAA ACA AAG GAT GCT TCC
Gly Pro Ala Glu Arg Ala Thr Thr Phe Ile Leu Phe Ala Asp Ser Tyr Leu Thr Gln Thr Lys Asp Ala Ser
        1220                                        1250                            1280
TAT GTC ACT GGT GAA CGT GCT ACA CTC AAG CCT ATC ATC GCT TTG AAG GAC TTG GAC TAT GTC GTC AAT GTC TGG TCT AAT GGC
Tyr Val Thr Gly Glu Arg Ala Thr Leu Lys Pro Ile Ile Ala Leu Lys Asp Leu Asp Tyr Val Val Asn Val Trp Ser Asn Gly
            1310                                              1340
TGT TTC GAT TTA TGG GAA GAA GTC AAC GGT GTT CAC TTC TAT ACT TTA ATG CGT ATG CGT AAG GGT TTG CTT
Cys Phe Asp Leu Trp Glu Glu Val Asn Gly Val His Phe Tyr Thr Leu Met Val Met Arg Lys Gly Leu Leu
```

Fig.2(c)

```
                                                                           1400                                   1430
CTT GGT GCA GAT TTC GCT AAA CGT AAC GGT GAC TCT ACT CGT GCA TCT ACC TAT AGC AGC ACT GCA TCC ACT
Leu Gly Ala Asp Phe Ala Lys Arg Asn Gly Asp Ser Thr Arg Ala Ser Thr Tyr Ser Ser Thr Ala Ser Thr
                            1460                                              1490
ATT GCA AAC AAG ATC TCT AGC TTC GTT TGG TCT TCT AAT AAC AGT CAA GTC AGT CAA AGC GTT ACT GGT
Ile Ala Asn Lys Ile Ser Ser Phe Val Trp Ser Ser Asn Asn Ser Gln Val Ser Gln Ser Val Thr Gly
              1520
GGT GTC AGT AAA AAG GGT TTG GAT GTC TCC ACA TTG TTG GCT CTT GGT AGT GTT GAT GAT GGA TTC
Gly Val Ser Lys Lys Gly Leu Asp Val Ser Thr Leu Leu Ala Leu Gly Ser Val Asp Asp Gly Phe
      1580                                     1605                                     1645
TTC ACT CCT GGC TCT GAA AAG gtaaattaac atgcataaaa gaataagact ataacattac taattcacat tttctactca g
Phe Thr Pro Gly Ser Glu Lys                                                                    INTRON
                                            1680                                         1710
ATC CTT GCC ACT GCT GTT GCT TCC TTC GAA GAC TCC TTG TAT CCT ATC AAC AAA AAC CTT CCA TCT
Ile Leu Ala Thr Ala Val Ala Ser Phe Glu Asp Ser Leu Tyr Pro Ile Asn Lys Asn Leu Pro Ser
                              1740                                                               1800
TAC CTT GGT AAC TCT ATT GGT AGA TAT CCT GAA GAC ACT TAC AAT GGA AAC TCT CAA GGA AAC TCT
Tyr Leu Gly Asn Ser Ile Gly Arg Tyr Pro Glu Asp Thr Tyr Asn Gly Asn Ser Gln Gly Asn Ser
                                                    1830                                         1860
TGG TTC GCT GTA ACT GGT TAC GCT GAG CTC TAT TAC CGT TAT AAG TTT GAT TCA TCT GGA AAG TAC GGT GGT
Trp Phe Leu Ala Val Thr Gly Tyr Ala Glu Leu Tyr Tyr Arg Tyr Lys Phe Asp Ser Ser Gly Lys Tyr Gly Gly
                                1890                                        1920
GTC ACT GTC AGC ATA AGT TTA CCC TTC TTC AAG TTT GAT TCA TCT GCT ACA TCT GGA AAG TAC
Val Thr Val Ser Ile Ser Leu Pro Phe Phe Lys Phe Asp Ser Ser Ala Thr Ser Gly Lys Tyr
                                    1950                                              1980                                2010
ACT GTT GGT ACC TCC GAC TTT AAC AAC CTT GCT CAA AAT ATT GCA CTC GCT GCT GAC CGT TTC TCC ACT
Thr Val Gly Thr Ser Asp Phe Asn Asn Leu Ala Gln Asn Ile Ala Leu Ala Ala Asp Arg Phe Ser Thr
```

Fig. 2(d)

```
                                                    2040                                                    2070
GTC CAG CTC CAT GCT CAC AAC AAT GGA TCT CTT GCT GAA GAG TTT GAC CGC ACC ACT GGT TTA TCC ACC GGT
Val Gln Leu His Ala His Asn Asn Gly Ser Leu Ala Glu Glu Phe Asp Arg Thr Thr Gly Leu Ser Thr Gly
        2100                                                    2130                                                    2160
GCT AGA GAC TTG ACC TGG TCT CAC GCT TCT TTA ATC ACC GCT TCT TAC GCT AAG GGT GCA CCT GCC GCT
Ala Arg Asp Leu Thr Trp Ser His Ala Ser Leu Ile Thr Ala Ser Tyr Ala Lys Gly Ala Pro Ala Ala
                                2190                                                    2230
TAAGCTGTAA ATTTAAATGC AAAGCATTAC AGCTTATTTT CTTTTTCAAA TAAAAACATA TTGATATGTT CATAACATTT TCTTGTT
                2270
TGT TGTACTGTAA TATGGGTAAC CACATAAGCA TAAACAGCAA
```

Fig. 3(a)

```
                                         50
        AAATT TATGTCAAGA ACATTGCTTA CTCCAAGAAG GTTACTGTAA TTTACGCCGA TGGCTCTGAC AACTGGAATA
100                                                    150
ATAATGGAAA CACCATTGCT GCTTCTTACT CTGCTCCTAT TTCTGGATCA AATTACGAAT ACTGGACATT CTCTGCCTCC ATTAATGGTA
                200                                                    250
TCAAGGAGTT CTACATTAAG TATGAGGTCA GTGGAAAAAC ATACTATGAT AACAACAATT CTGCCAATTA CCAAGTATCT ACATCCAAGC
                        300                                                    350
CTACTACTAC TACTGCTACT CTACCGCTCT TTCCACTTCA ACCACGACTC CCCCCTCAAG CTCTGAGCCA GCTACTTTCC
                                400                                                    450
CAACTGGTAA CTCTACAATC TCCTCATGGA TTAAGAAGCA AGAAGGTATC AGCCGCTTTG CTATGCTTCG AAACATCAAT CCTCCTGGAA
                                        500                                                    
GCGCTACCGG TTTCATTGCT GCCTCACTCT CTACCGCTGG TCCCGATTAC TACTATGCTT GGACTCGTGA TGCTGCATTA ACCTCCAATG
        550                                                    600
TAATTGTTTA CGAATACAAC ACTACTTTGT CCGGTAATAA GACTATCCTC AACGTCCTCA AGGACTATGT TACATTCTCA GTCAAGACCC
                650                                                    700
AATCAACTTC TACCGTCTGT AACTGCCTTG GTGAGCCTAA GTTCAATCCT GATGGTTCTG GCTATACTGG TGCTTGGGGA AGACCTCAAA
                        750                                                    800
ATGATGGACC TGCTGAACGT GCTACTACCT TCATTTTGTT TGCTGACAGT TATCTTACTC AAACAAAGGA TGCTTCCTAT GTCACTGGTA
                                850                                                    900
CACTCAAGCC TGCTATCTTC AAGGACTTGG ACTATGTCGT CAATGTCTGG TCTAATGGCT GTTTCGATTT ATGGGAAGAA GTCAACGGTG
```

Fig. 3(b)

```
                                                        950
TTCACTTCTA TACTTTAATG GTTATGCGTA AGGGTTTGCT TCTTGGTGCA GATTTCGCTA AACGTAACGG TGACTCTACT CGTGCATCTA
         1000                                                    1050
CCTATAGCAG CACTGCATCC ACTATTGCAA ACAAGATCTC TAGCTTCTGG GTTTCTTCTA ATAACTGGAT TCAAGTCAGT CAAAGCGTTA
CTGGTGGTGT CAGTAAAAAG GGTTTGGATG TCTCCACATT GTTGGCTGCT AACCTTGGTA GTGTTGATGA TGGATTCTTC ACTCCTGGCT
         1100                                                    1150
CTGAAAAGAT CCTTGCCACT GCTGTTGCTG TTGAAGACTC CTTCGCTTCC TTGTATCCTA TCAACAAAAA CCTTCCATCT TACCTTGGTA
                                                         1250
ACTCTATTGG TAGATATCCT GAAGACACTT ACAATGGTAA CGGAAACTCT CAAGGAAACT CTTGGTTCTT GGCTGTAACT GGTTACGCTG
         1450                                       1400                                     1350
AGCTCTATTA CCGTGCCATC AAGGAATGGA TCGGCAACGG TGGTGTCACT GTCAGCAGCA TAAGTTTACC CTTCTTCAAG AAGTTTGATT
CATCTGCTAC ATCTGGAAAG AAGTACACTG TTGGTACCTC CGACTTTAAC AACCTTGCTC AAAATATTGC ACTCGCTGCT GACCGTTTCT
                                                    1600                                     1500
TGTCCACTGT CCAGCTCCAT GCTCACAACA ATGGATCTCT TGCTGAAGAG TTTGACCGCA CCACTGGTTT ATCCACCGGT GCTAGAGACT
         1650                                              1700
TGACCTGGTC TCACGCTTCT TTAATCACCG CTTCTTACGC TAAGGCTGGT GCACCTGCCG CTTAAGCTGT AAATTTAAAT GCAAAGCATT
ACAGCTTATT TTCTTTTTCA AATAAAAACA TATTGATATG TTCATAACAA AAAAAAAAAA
         1750
``` ness of 4,863,864

GLUCOAMYLASE GENE OF RHIZOPUS ORYZAE

FIELD OF THE INVENTION

The present invention relates to the Rhizopus derived glucoamylase gene, a novel recombinant vector comprising said gene, and a microorganism transformed by said vector. The present invention also relates to a process for producing Rhizopus glucoamylase by cultivating the transformed microorganism, especially yeast, in a liquid medium.

PRIOR ART

Cloning of glucoamylase genes from *Aspergillus niger* (The EMBO Journal, vol. 3, no. 5, pp. 1097–1102, 1984) and from *Aspergillus awamori* (Yeast Genetics and Molecular Biology Abstracts, pp. 142, 1984) has already been reported.

Glucoamylase (EC 3.2.1.3) is an enzyme that hydrolyzes the α-1,4-glucoside chain progressively from the non-reducing terminal end. This enzyme also hydrolyzes the α-1,6-glucoside chain. Glucoamylase is secreted from fungi of the genera Aspergillus, Rhizopus and Mucor and is used in glucose production and quantitative determination of glycogen and starch. One of its major applications is that of its use as a saccharifying agent in the production of ethyl alcohol from starchy materials. The glucoamylase derived from the genus *Rhizopus* is produced in particularly high productivity and enzymatic activity. Furthermore, in comparison with the glucoamylase derived from other organisms, the Rhizopus-derived glucoamylase exhibits a strong action on raw starch and its enzymological and chemical properties including optimum pH are particularly suitable for the saccharification of cereal starch. Because of these features, the Rhizopus-derived glucoamylase is considered to be best suited to alcohol production by using non-cooked or low-temperature cooked starch (see U.S. Pat. No. 4,514,496 and 4,092,434).

One problem with the production of Rhizopus glucoamylase is that high enzymatic activity can be obtained only by employing cultivation on a solid medium using wheat bran as the principal substrate. This increases the cost of enzyme production and, hence, alcohol production as compared with the Aspergillus derived enzyme which can be produced by cultivation in a liquid medium. Furthermore, the glucoamylase produced by the genus Rhizopus undergoes partial degradation by protease and may lose the efficiency required to hydrolyze raw starch.

SUMMARY OF THE INVENTION

One object of the present invention is to realize a method of production of glucoamylase that is inexpensive and is suitable for manufacturing alcohol.

Another object of the present invention is to provide a glucoamylase gene, particularly one derived from a fungus of the genus Rhizopus, that is capable of expression in the yeast used for alcohol production from starchy materials, such as cereals, by the non-cooking or low-temperature cooking process.

A further object of the present invention is to provide a vector comprising said gene, and a microorganism such as yeast transformed by such vector, particularly a transformed microorganism that can be cultured in a liquid medium add A still further object of the present invention is to provide a process for producing a Rhizopus-derived glucoamylase without undergoing degradation by protease.

BRIEF DESCRIPTION OF THE DRAWINGS

FIG. 1 shows the nucleotide sequence of the intron-free glucoamylase structural gene of the invention together with the signal peptide region;

FIG. 2 shows the nucleotide sequence of a glucoamylase gene cloned from the chromosomal DNA of *Rhizopus oryzae;*

FIG. 3 shows the nucleotide sequence of the C-terminal region of a glucoamylase gene cloned from the cDNA obtained from the mRNA of *Rhizopus oryzae;*

FIGS. 5, 6A, 6B and 6C are flowsheets showing the steps for constructing, in a plasmid vector, an intron-free cDNA of the complete length by conjugating the two genes shown in FIG. 4, and for incorporating a promoter and a tail with a view to ensuring efficient gene expression in yeast, wherein FIG. 5 shows the steps for producing pCGA469, FIG. 6A illustrates the steps for producing pYGA2149 and pYGA2169, FIG. 6B depicts the steps for producing pYGIFLm222 (the lined sections and the cross-hatched sections of FIG. 6B represent structural genes for gamma-interferon and glyceraldehyde-3-phosphate dehydrogenase, respectively) and FIG. 6C depicts the steps for producing pYGA2269 and pYGA195;

DETAILED DESCRIPTION OF THE INVENTION

Figure 4:
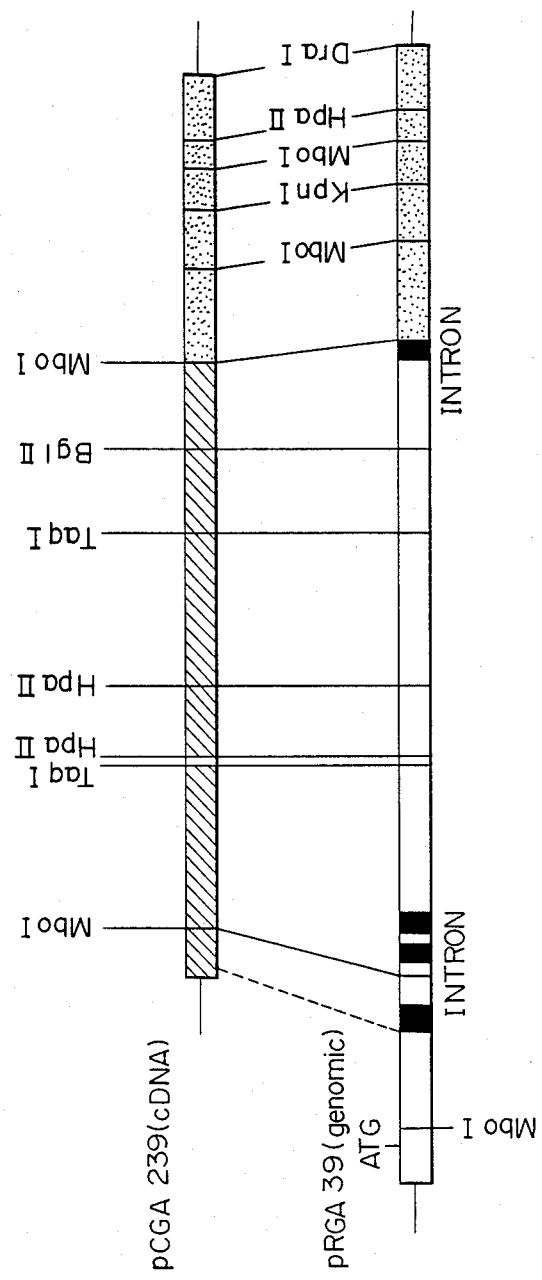
FIG. 4 compares the glucoamylase gene cloned from the chromosomal DNA of *Rhizopus oryzae* with the glucoamylase gene prepared from the mRNA of *Rhizopus oryzae* (the lined section of pCGA239 in FIG. 4 represents a portion of the glucoamylase-encoding cDNA which corresponds to the intron-containing portion of the genomic glucoamylase gene in plasmid pRGA39; each of the dotted sections of pCGA239 and pRGA39 represents a portion of the glucoamylase-encoding gene wherein the DNA sequences in pCGA239 and pRGA39 are identical; the broken line in the left of FIG. 4 represents the site of in vitro mutagenesis which is described in FIG. 5)

The present inventors have for the first time isolated a glucoamylase gene from a fungus of the genus Rhizopus and determined its structure. The present inventors then prepared from this gene vectors capable of expression in *E. coli* or yeast, and used the vectors in transforming such microorganisms. The inventors confirmed that the transformed microorganisms actually produced glucoamylase and were capable of direct production of alcohol from non-cooked raw starchy materials or low-temperature cooked starchy materials. The inventors also confirmed that the glucoamylase produced by such transformed microorganisms exhibited high ability to hydrolyze raw starch since it was not exposed to degradation by the Rhizopus-produced protease.

The present invention has been accomplished on the basis of these findings.

Any fungi of the genus Rhizopus that are capable of producing glucoamylase may be used in the present invention for obtaining the desired gene. Illustrative species include *Rhizopus oryzae, Rhizopus formosaensis, Rhizopus javanicus* and *Rhizopus thailandensis.* The present inventors have confirmed that *Rhizopus oryzae* SAM0034 (FERM P-7960; FERM BP-929) produces a glucoamylase particularly suitable for hydrolyzing raw starch.

The present strain (SAM0034) has the following mycological properties.

Colonies on Potato dextrose agar medium attaining a diameter of 5-5.5 mm in one day at 28° C. and covering 90 mm petri plates of Potato dextrose agar medium in two days, white. Colonies becoming grey with age.

Stolons hyaline or yellowish brown; rhizoids brown. Sporangiophores usually arising from rhizoids, occasionally arising directly from stolons, either single or in groups, occasionally divided, 220-1200 μm long. Sporangia globose or subglobose, dark brown, 60-150 μm in diameter; columellae globose or subglobose. Sporangiospores globose, subglobose, or angular, striatae on the surface, 5-15×3-7 μm. Chlamydospores subglobose or cylindrical, 6-13×4-19 μm. No zygospores were observed. At 37° C., growth occurs.

The present strain (SAM0034) can be accommodated in the fungus genus Rhizopus, because: (1) the sporangiospores are produced within the columellate sporangium; (2) the sporangiospores are brown; and (3) The rhizoids are produced.

The mycological properties of the present strain (SAM0034) were compared with those of the known species of the genus Rhizopus, referring to Inui, T., Y. Takeda & H. Iizuka, 1965. Taxonomical Studies on Genus Rhizopus (Journal of General and Applied Microbiology, Vol. 11, Supplement, 121 pp. Zycha, H., R. Siepmann & G. Linnemann, 1969. Mucorales. Eine Beschreibung aller Gattungen und Arten dieser Pilzgruppe. 335 pp. J. Cramer, Lehre. Domsch, K. H., W. Gams and T. H. Anderson, 1980. Compendium of Soil Fungi, Vol. 1, 859 pp. Academic Press. London). The result of this comparison revealed that the present strain could be identified as *Rhizopus oryzae,* because: (1) the present strain can grow at 37° C.; (2) the sporangiospores are striate and measure 5-15×3-7 μm; (3) the sporangiophores measure 220-1200 μm in length; and (4) the sporangia measure 60-150 μm in diameter.

Glucoamylase gene

The glucoamylase gene of the present invention has the nucleotide sequence shown in the brackets in FIG. 1. The glucoamylase gene may be isolated in the form of cDNA prepared from the mRNA of Rhizopus or by cloning from the chromosomal DNA of Rhizopus using a synthetic origonucleotide corresponding to a part of amino acid sequence of Rhizopus glucoamylase.

Usually it is not easy to obtain the complete glucoamylase gene by the former method, while the gene obtained by the latter method usually contains intron sequences and thus cannot be expressed in host *E. coli* or yeast. In order to obtain a glucoamylase gene capable of expression in these hosts, an appropriate part of the cDNA from mRNA may be conjugated with the intron-free part of the DNA sequence of the chromosomal gene. If one or both DNA fractions lack suitable sites to be cleaved by restriction enzymes, a technique of in vitro mutagenesis may be employed to introduce suitable cleavage sites for conjugation purposes.

The scope of the glucoamylase gene of the present invention involves not only the same nucleotide sequence coding for the bracketed amino acid sequence in FIG. 1 but also a nucleotide sequence corresponding to an amino acid sequence having an enzymatic activity comparable to that of the bracketed amino acids.

The Rhizopus-derived glucoamylase structural gene is a DNA fragment encoding the sequence of 26-604 amino acids from the N-terminal in FIG. 1, or it corresponds to nucleotide sequence numbers 190-1926 designated in FIG. 1. The region of 1-25 amino acids from the N-terminal is a signal peptide coding region involved in the extracellular secretion of glucoamylase from the host cell. When, as described below, glucoamylase was produced by a yeast using this signal peptide coding region, more than 90% of the glucoamylase produced was secreted in the culture medium. The secreted glucoamylase was purified by routine method and the amino acid sequence at the N-terminus was examined; the amino acid sequence of the glucoamylase started at the 26th amino acid of the sequence given in FIG. 1 and this indicates that the region defined by 1-25 amino acids from the N-terminus will function as a signal peptide in a yeast as well.

Therefore, if a signal sequence coding for the following amino acid sequence:

| MET | GLN | LEU | PHE | ASN | LEU | PRO | LEU | LYS | VAL | SER |
|-----|-----|-----|-----|-----|-----|-----|-----|-----|-----|-----|
| PHE | PHE | LEU | VAL | LEU | SER | TYR | PHE | SER | LEU | LEU |
| VAL | SER | ALA | | | | | | | | | is combined with a DNA fragment coding for a suitable proteinaceous substance (e.g. interferons, lymphokines and interleukine 2) in a DNA expression vector and if this vector is used to transform a suitable host, the desired proteinaceous substance can be excreted extracellularly.

A method that can be used with advantage for the purpose of isolating the glucoamylase gene shown above is described hereunder. The whole DNA is separated from a glucoamylase-producing fungus of the genus Rhizopus by a modified version of the method of Cryer et al. The microorganism is first sporulated and the spores produced are collected. The chromosomal DNA can be prepared from the fungal spores by first disrupting them with glass balls as will be described below in Example 1 (a-i), the mixture is then extracted using the method of Cryer et al., Methods in Cell Biology, 12, 39–44, 1975, and the extract is and are finally subjected to gel filtration. The resulting DNA fraction is digested with HindIII and cloned to the HindIII site of a known vector pBR322 to obtain a Rhizopus gene library in *E. coli.* The library may be recovered in the form of an ampicillin-resistant transformant.

A probe (DNA oligomer) described in Examples 1 and 2 for detecting the glucomylase gene is prepared and used in colony hybridization. Colonies that will hybridize with the probe are grown and the plasmid DNA is extracted.

The gene of the present invention can be incorporated in a suitable plasmid vector and have been expressed in a host microorganism such as yeast or *Bacillus subtilis* in the production of the Rhizopus glucoamylase and alcohol. Therefore, the present invention also relates to the plasmid vector comprising the aforementioned glucoamylase gene, as well as a microorganism (e.g. yeast and *Bacillus subtilis*) transformed by such vector.

In order that the glucoamylase gene is expressed in a microorganism, it is preferred that a promoter and/or a tail (3' non-translational area) suitable for that microorganism is used (see Unexamined Published Japanese patent application No. 146281/1983). For example, in order to have the glucoamylase gene expressed in a yeast, the promoter region ($P_{GAP}$) and tail region ($T_{GAP}$) of the glyceraldehyde-3-phosphate dehydrogenase gene (GAP-DH), the promoter region (Ppho5) of the acid phosphatase gene (PHO5), and the promoter region ($P_{PGK}$) of the 3-phosphoglycerokinase (PGK) may be employed as shown in Examples 1 and 2. A plasmid vector comprising these promoter and/or tail region together with the gene of the present invention, as well as a microorganism transformed by such vector are preferred embodiments of the present invention.

The present invention is hereunder described in greater detail with reference to the following examples.

EXAMPLE 1

(a-i)

DNA preparation and its cloning

The whole DNA was isolated from glucoamylase-producing *Rhizopus oryzae*. DNA isolation was performed by a modified version of the method of Cryer et al. that was described in Method in Cell Biology, vol. 12, pp. 39-44, 1975 and originally employed with yeasts. A thin potato slice was sterilized in an autoclave and the cells of *Rhizopus oryzae* were grown for sporulation. The spores produced were collected, suspended in a solution of 0.15M NaCl and 0.05M EDTA, and disrupted by treatment for 15 seconds in a Dyno mill using glass balls. Subsequent procedures were the same as those employed in the method of Cryer et al., except that in the last step, gel filtration using Biogel $A_{5m}$ (the tradename of Bio-Rad for a molecular sieve) was performed to isolate the whole DNA. This DNA fraction was digested with HindIII and cloned to the HindIII site of pBR322 to obtain a Rhizopus gene library in *E. coli* strain WA802. The strain was transformed by a routine method. The library was obtained as an ampicillin-resistant transformant.

(a-ii)

Selection of transformant and characteristics of the glucoamylase gene

Transformant selection was made by a method generally referred to as colony hybridization, using a nitrocellulose filter paper. The first step starts with the preparation of a probe for detecting the glucoamylase DNA. For this purpose, the purified Rhizopus glucoamylase was decomposed by a variety of proteases and the resulting peptides were separated and purified. These peptides were subjected to amino acid analysis and the primary structures were determined by routine methods. As a result, an amino acid sequence having the partial structure of Asp-Leu-Thr-Trp-Ser-His-Ala-Ser was obtained. It was also found that this glucoamylase had an N-terminal amino acid sequence of Ala-Ser-Ile-Pro and a C-terminal sequence of Ala-Ala. In order to prepare the desired probe, 32 different synthetic DNA oligomers each consisting of 14 bases (5'-ACNTGGTCNCAQGC-3') were produced by the triester solid-phase method from the amino acid sequence of Thr-Trp-Ser-His-Ala which was part of the sequence identified above and wherein N is an arbitrary base and Q is T or C from pyrimidine. These DNA oligomers were labelled with [$\gamma^{32}$p]ATP and T4-polynucelotidyl kinase and used as probes for detecting the glucoamylase gene. Transformed *E. coli* colonies that hybridized with these probes by colony hybridization were grown and plasmid DNAs were extracted. The extract was treated with restriction enzymes and the resulting DNA fragments were analyzed by agarose-gel electrophoresis. As for the colonies that hybridized with the probes, the DNA fragment inserted in the plasmid had a size of 4.3 kb, as well as one cleavage site each of BamHI, KpnI, MluI and SacI, two sites for DraI and three sites for BglII, but had no cleavage sites for AccI, BalI, ClaI, EcoRI, HpaI, PstI, PvuII, ScaI or XhoI. The plasmid having this DNA fragment was named pRGA39.

(b-i) RNA preparation and cDNA cloning

The whole RNA was isolated from the aerial hyphae of *Rhizopus oryzae*. For this purpose, known procedures including the use of guanidium thiocyanate were followed. Polyadenylated RNA was recovered from the whole RNA as a mRNA fraction by way of chromatography on oligo-dT cellulose. Using this mRNA, a cDNA gene library was formed in *E. coli* WA802 by the method of Okayama and Berg described in Okayama, H. & Berg, P., Mol. Cell Biol., 2, 161, 1982.

(b-ii)

Transformant selection and characterization of glucoamylase cDNA

Selection of the transformant having the c-DNA of the aimed enzyme was made by the aforementioned method of colony hybridization. A DraI fragment (2.0 kb) of the glucoamylase gene obtained in (a-ii) was used as a probe for detecting the glucoamylase cDNA. For this purpose, this fragment was labelled by the technique of nick translation using [$\alpha$-$^{32}$P]dCTP, DNA polymerase I and DNase I. The transformed colonies that would hybridize with this probe were allowed to grow and the plasmid DNA was extracted. The extract was treated with restriction enzymes and the resulting DNA fragments were analyzed by electrophoresis on agarose gel. The DNA fragment which had been inserted into the plasmid of the colonies that hybridized with the probe had a size of 1.7 kb. This plasmid was named pCGA239.

(c)

Nucleotide DNA sequence analysis

Plasmids pRGA39 and pCGA239 were digested with restriction enzymes and DNA fragments were isolated on agarose gel. Their nucleotide sequences were determined by the dideoxy method using recombinant phage M13. Analysis of pRGA39 revealed that this gene contained four introns each having a length of several tens of bp (for the intron sites, see FIG. 2). The plasmid pCGA239 was not a cDNA corresponding to the full length of glucoamylase but lacked about 50 amino acids. Restriction maps of pRGA39 and pCGA239 are compared in FIG. 4.

(d)

Construction of glucoamylase gene to be expressed

Figure 5:
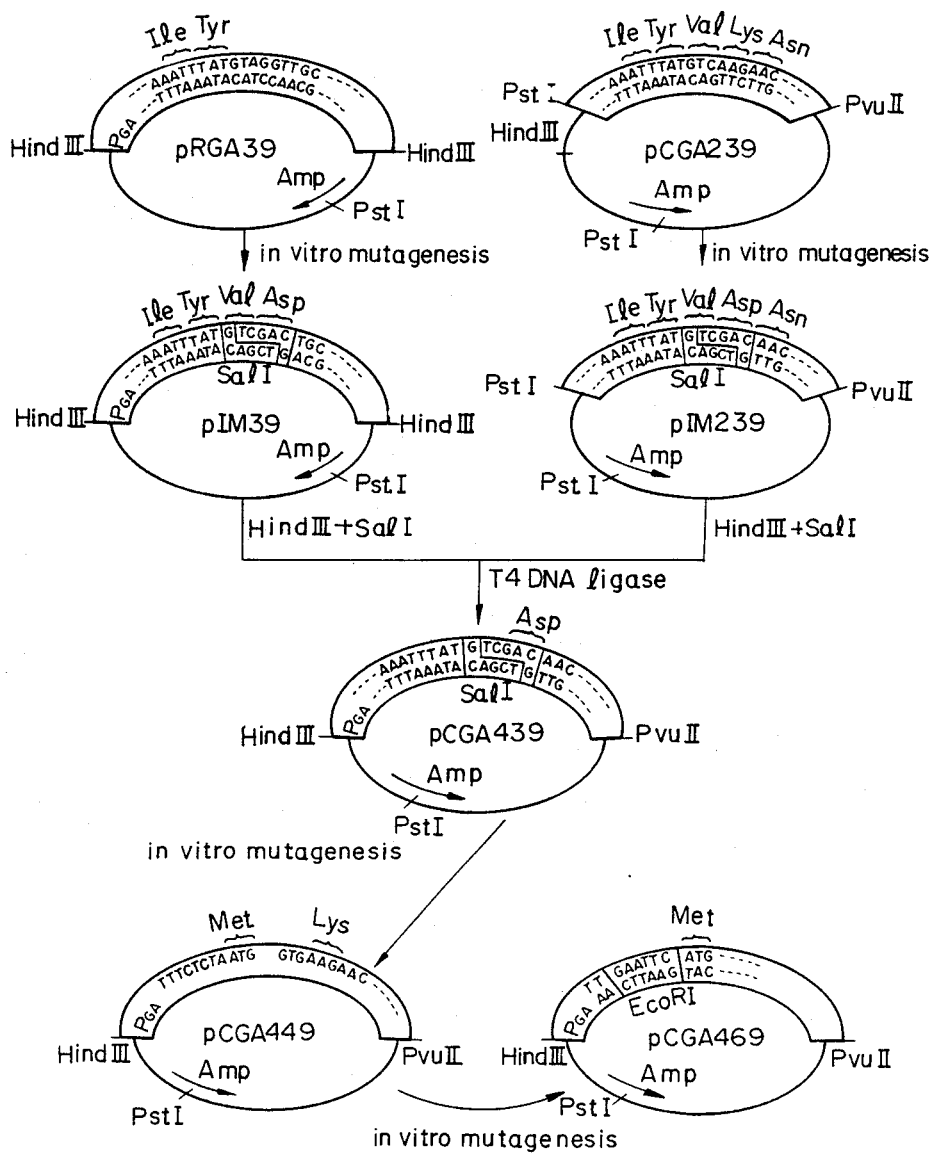

The cloned recombinant DNA did not have the full length. A cDNA of the full length having in addition a glucoamylase promoter (derived from Rhizopus) was prepared by conjugating appropriate parts of pCGA239 and pRGA39. Since suitable restriction sites available for conjugation purposes were absent from the plasmids, the SalI site was introduced at the corresponding locations of pCGA239 and pRGA39 by the method of in vitro mutagenesis before performing the conjugation (see FIG. 5). For the method of in vitro mutagenesis, see Morinaga, Y. et al., BIO/TECHNOLOGY, 2, 636–639 (1984).

Because of the introduction of the SalI site, the 53rd amino acid codon from the N-terminal of the treated plasmid pCGA439 was aspartic acid rather than lysine which was initially present. Therefore, the plasmid was again subjected to in vitro mutagenesis, whereby plasmid pCGA449 (deposited in the FRI under accession number FERM BP-673) containing glucoamylase DNA of the full length having the inherent nucleotide sequence was obtained. This plasmid has been deposited with the Fermentation Research Institute, the Agency of Industrial Science and Technology, under designation of SAM0039 in accordance with the Budapest Treaty and has been assigned accession number FERM BP-673.

The full-length glucoamylase gene in pCGA449 is the combination of the sequence appearing before the arrow in FIG. 2(a) and the sequence appearing after the arrow in FIG. 3.

(e)

Construction of expression vector in yeast (e-i)

Figure 6A:
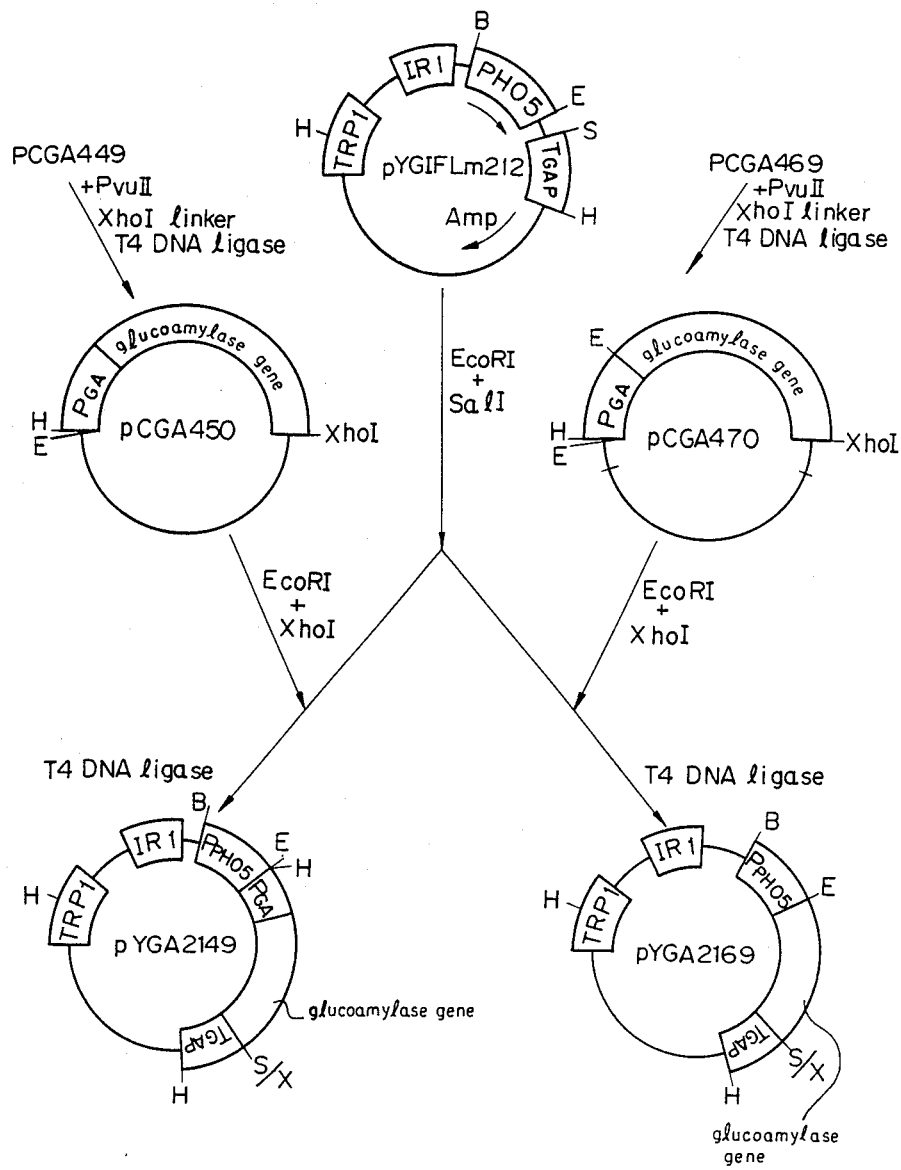

With a view to ensuring efficient expression of pCGA449 in a yeast, a fragment (ca. 8.3 kb) cut out with EcoRI-SalI from pYGIFLm212 FERM BP-2216 having the acid phosphatase promoter (Ppho5) disclosed in Japanese patent application No. 157037/1984 (FRI accession number FERM BP-7727 and FERM BP-383) was used. In order to incorporate pCGA449 at the EcoRI-SalI site, the PvuII site of pCGA449 was converted to XhoI site with XhoI linker, whereby plasmid pCGA450 was prepared (FIG. 6A). This plasmid was cleaved with XhoI and EcoRI and a 2.2 kb fragment was separated by agarose gel electrophoresis. This fragment was ligated to the previously obtained 8.3 kb EcoRI-SalI fragment with a T4-DNA ligase. The resulting plasmid containing Ppho5 as a promoter was named pYGA2149. This plasmid was grown in E. coli strain WA802 and then separated (see FIG. 6A).

(e-ii)

Figure 6B:
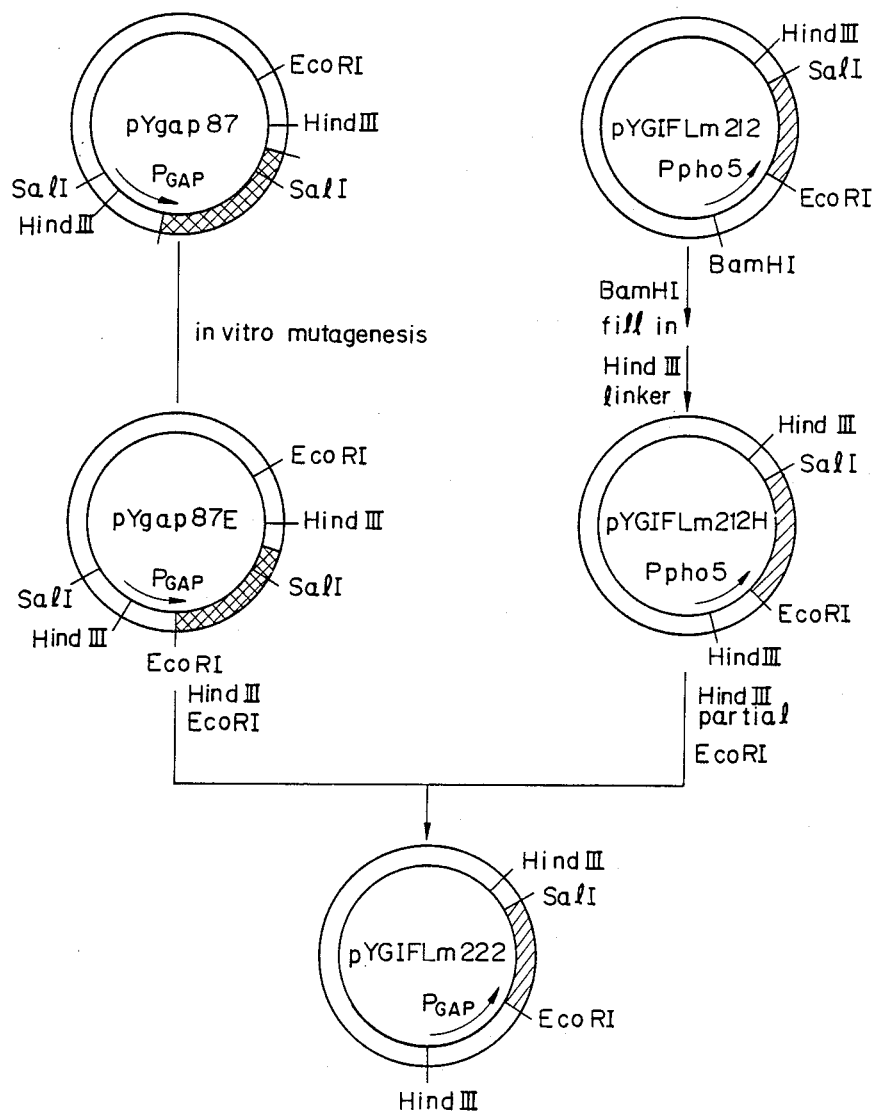
Figure 6C:
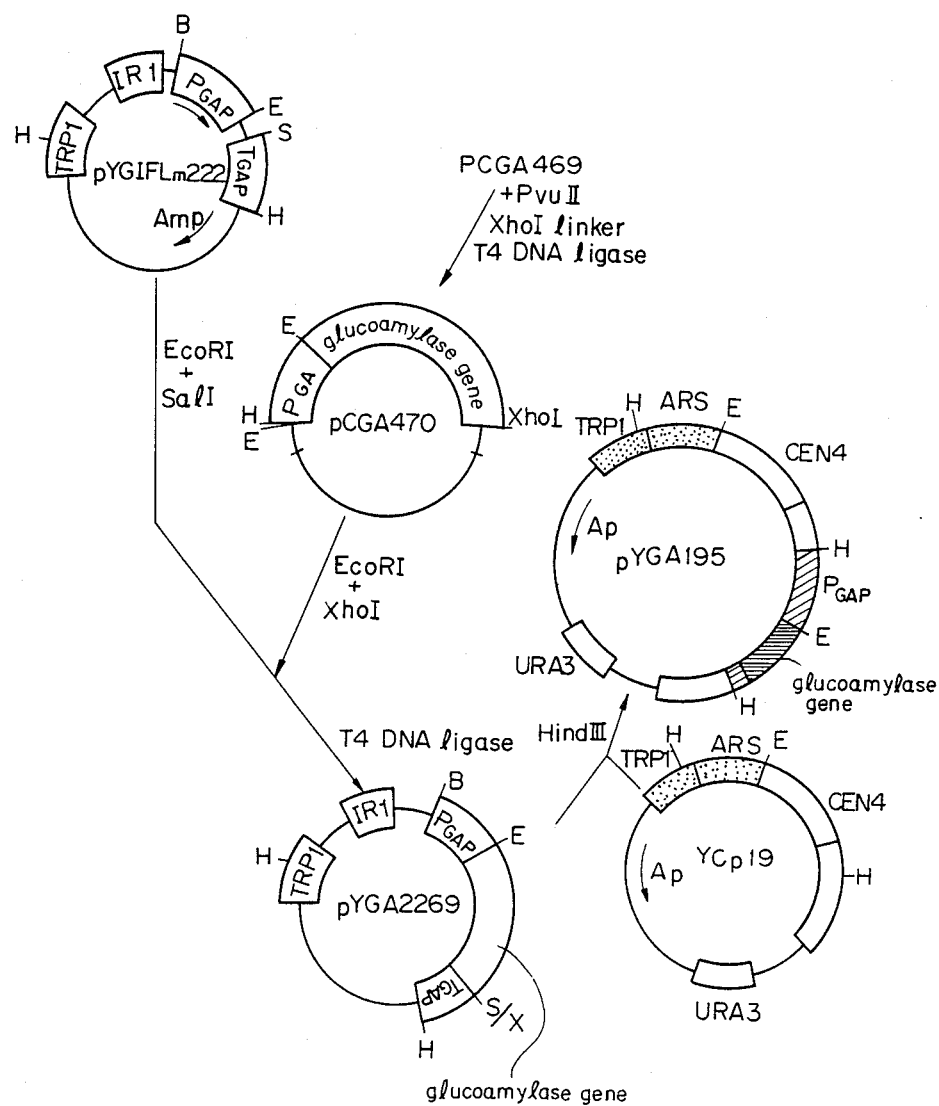

With a view to ensuring efficient expression of pCGA469 in a yeast, a fragment (ca. 8.9 kb) cut out with EcoRI-SalI from pYGIFLm222 having the glyceraldehyde-3-phosphate dehydrogenase promoter ($P_{GAP}$) disclosed in Japanese patent application No. 184291/1982 was used. In order to incorporate pCGA469 at the EcoRI-SalI site, the PvuII site of pCGA469 was converted to an XhoI site with a XhoI linker, whereby plasmid pCGA470 was prepared (FIG. 6C). This plasmid was cleaved with XhoI and EcoRI and a 2.2 kb fragment was separated by agarose gel electrophoresis. This fragment was ligated to the previously obtained 8.9 kb EcoRI-SalI fragment with a T4-DNA ligase. The resulting plasmid containing $P_{GAP}$ as a promoter was named pYGA2269. This plasmid was grown in E. coli strain WA802 and then separated (see FIG. 6C). The plasmid pYGIFLm222 used above was prepared (FIG. 6B) by replacing the expression promoter Ppho5 in pYGIFLm212 with a glyceraldehyde-3-phosphate dehydrogenase promoter ($P_{GAP}$: see Japanese patent application No. 184291/1982). Detailed procedures were as follows: the unique BamHI site in pYGIFLm212 was cleaved with BamHI, filled in with DNA polymerase I, and treated with a HindIII linker to convert the BamHI site to a HindIII site, whereby plasmid pYGIFLm212H was obtained. Using the technique of in vitro mutagenesis, an EcoRI site was introduced into pYgap87 (FERM BP-382) (deposited in the FRI under accession number FERM BP-382) immediately upstream from ATG (the initiation codon for the replication of the structural gene of glyceraldehyde-3-phosphate dehydrogenase), whereby plasmid pYgap87E was prepared. The plasmid pYGIFLm212H was cleaved with EcoRI, further cleaved partially with HindIII and then subjected to agarose gel electrophoresis to isolate an 8.0 kb fragment. The plasmid pYgap87E was cut with EcoRI and HindIII and subjected to agarose gel electrophoresis to isolate a 1.1 kb fragment. This fragment was ligated with the foregoing 8.0 kb fragment of pYGIFLm212H and the resulting recombinant plasmid pYGIFLm222 was recovered from the transformed E. coli.

pYGA2169 was prepared from pYGIFLm212 using pCGA469 and repeating the same procedures as described above and the plasmid was separated (FIG. 6A).

pYGA2249 (not shown) was also prepared by the same procedures as described above and separated.

(f)

Expression of the glucoamylase gene in yeast

The plasmid pYGA2149 was used to transform yeast [Saccharomyces cerevisiae strains XS-30-2A (MATα, leu2, his3, trpl, ura3) and XS-30-2B (MATα, leu2, his3, trpl, ura3)] and the transformed colonies were selected on the basis of the nutrient requirement for tryptophan as a marker. Transformation was performed by the method of Ito et al. (Ito, H. et al., J. Bacteriol., 153, 1983) using LiCl. A platinum loopful of the transformed colonies were inoculated in 5 ml of YPD (yeast extract-polypeptone-dextrose medium) medium (1% yeast extract, 2% polypeptone and 2% glucose) and sampling was made 48 hours later. Centrifugation (10,000 rpm × 5 min) was conducted in an Eppendorf tube thus separating the sample into the supernatant and pellet. The activity of glucoamylase in the supernatant was measured by the following procedures: 200 μl of the supernatant was added to 800 μl of a soluble starch solution (1.0% soluble starch in 20 mM acetate buffer solution, pH 5.0) and the mixture was left to stand at 37° C. The amount of released glucose was determined with a glucostat (Fujisawa Pharmaceutical Co., Ltd.). The activity data for the 2-hour reaction were as follows: 0.004 U/ml for pYGA2149 in XS-30-2A and 0.008

Figure 7:
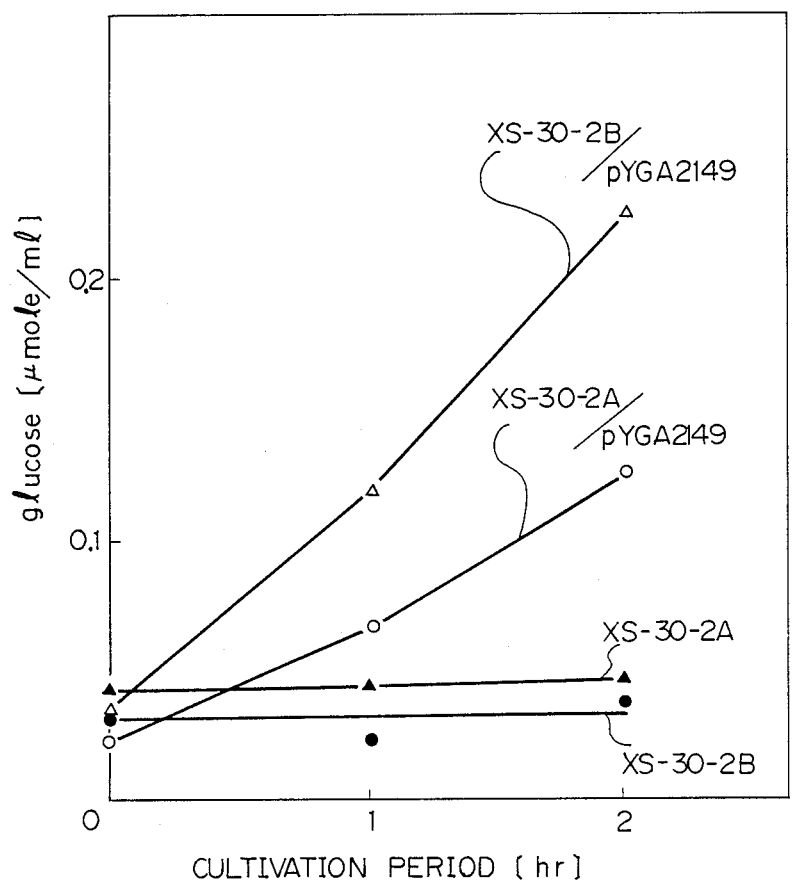
FIG. 7 is a graph showing the profile of glucoamylase production using transformed yeasts as performed in Example 1.

U/ml in XS-30-2B, indicating the sex-dependent difference by a factor of 2 (see FIG. 7). Activity of one unit (U) corresponds to 1 μmol of glucose released in 1 minute. No activity was observed in the supernatants obtained from yeast which did not contain pYGA2149.

The glucoamylase activity for the plasmid using $P_{GAP}$ as a promoter was 0.40 U/ml, which was 50-100 times the value for the case where such promoter was absent. The glucoamylase activity for the plasmid using the acid phosphatase gene promoter Ppho5 was dependent on the phosphate concentration of the medium. For example, no glucoamylase activity was observed after 48-hour cultivation in the ordinary YPD medium at 30° C., but an activity comparable to that for the use of $P_{GAP}$ appeared when the medium was replaced with YPD medium from which phosphate had been removed by treatment with magnesium sulfate and ammonia water (Rubin, G. M., Eur. J. Biochem., 41, 197-202, 1974). The supernatant from the culture was subjected to SDS-polyacrylamide gel electrophoresis and no less than 50% of the total extracellular protein was glucoamylase protein.

Figure 8:
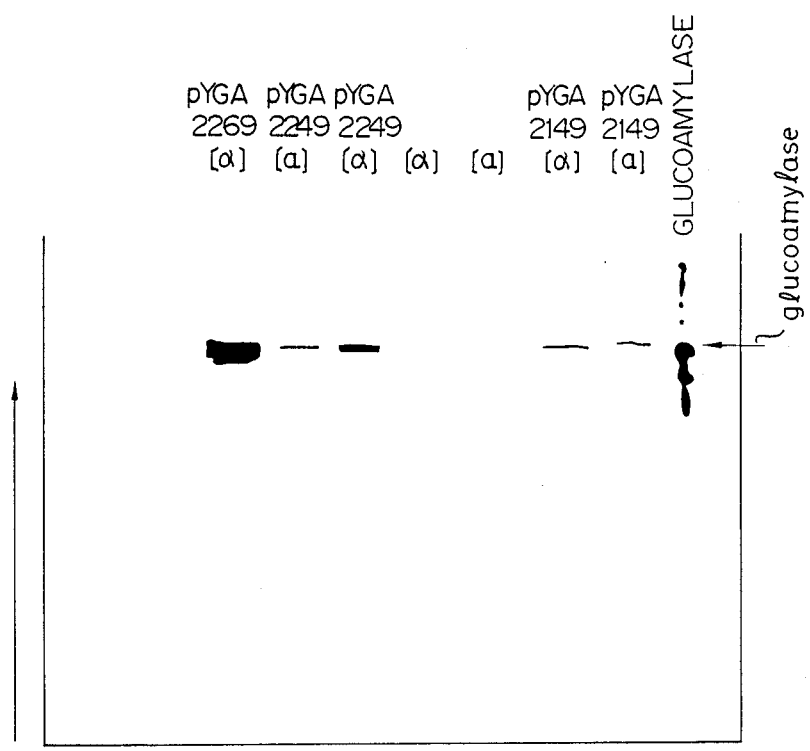
FIG. 8 is an electrophoretic diagram for glucoamylase samples produced by the transformed yeasts in Example 1.

It was confirmed by the following immunological techniques that the activities listed above were due to the Rhizopus-derived glucoamylase. A rabbit antibody was prepared using a purified glucoamylase. This antibody was used in the analysis by a method commonly referred to as Western blotting, using a concentrate of 1.5 ml of the same supernatant from the 48-hour culture that was employed in the previous activity measurements. One third portion of the concentrate was subjected to 10% polyacrylamide electrophoresis and the protein in the gel was transferred and immobilized on a nitrocellulose filter paper electrophoretically. The glucoamylase on the nitrocellulose filter paper was then detected by the known technique in enzyme immunology using the reaction with peroxidase. A band that would react with the glucoamylase antibody emerged at a position substantially equal to the Rhizopus glucoamylase in terms of molecular weight. This fact did indicate the expression of the Rhizopus-derived glucoamylase in yeasts. The data showing this fact are give in FIG. 8.

(g)

Growth of yeast using starch as a sole carbon source

Figure 9:
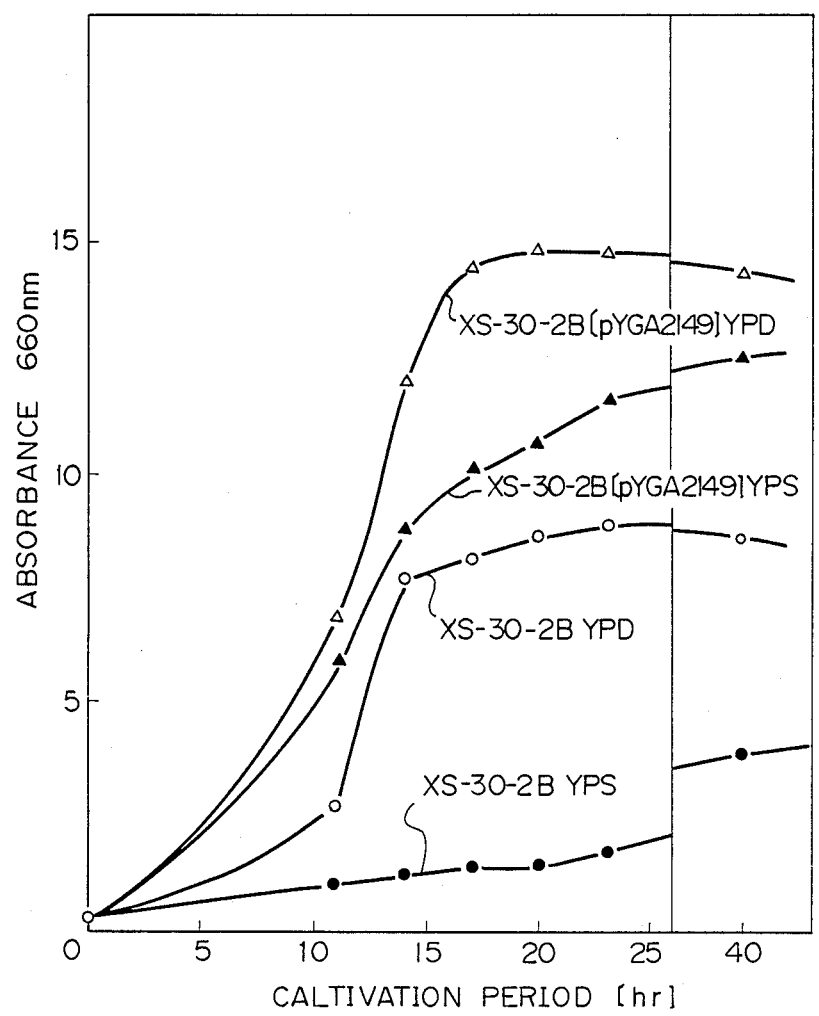
FIG. 9 is a graph showing growth curves for transformed yeasts that were cultured in Example 1 using starch as a sole carbon source.

The effect of pYGA2149 on the growth of yeast strain XS-30-2B was investigated using different carbon sources. First, XS-30-2B was shake-cultured in VPD medium for 24 hours at 30° C. and XS-30-2B (pYGA2149) was shake-cultured under the same conditions in a minimum nutrient medium (0.67% Difco Yeast nitrogen base and 2% glucose) containing 1% Casamino acids and uracil. A 100-ml portion each of YPD medium or YPS medium (1% yeast extract, 2% polypeptone and 2% soluble starch) was added in a 500-ml Sakaguchi flask and sterilized in an autoclave. Each of the pre-culture suspensions (1 ml) was added to these mediums at 30° C. and the subsequent growth was evaluated in terms of absorbance at 660 nm. The strain XS-30-2B harboring no plasmid pYGA2149 was capable of little growth in the YPS medium, but the strain harboring pYGA2149 grew at equal rates on both YPS and YPD mediums. This fact clearly shows that XS-30-2B (pYGA2149) produced glucoamylase and utilized the starch hydrolyzed by the enzyme (see FIG. 9).

(h)

Alcohol production by transformed yeasts (h-i)

Alcohol fermentation with soluble starch

The medium used in this experiment was prepared by autoclaving (121° C., 15 minutes) 200 ml of YPS medium (1% yeast extract, 2% polypeptone, and 1, 2 or 5% soluble starch) in a 500-ml Erlenmeyer flask. The following yeast strains were employed.

(1) XS-30-2B (control having no glucoamylase gene);
(2) XS-30-2B (transformed by pYGA2149) having a Rhizopus promoter;
(3) XS-30-2B (transformed by pYGA2169) having the promoter Ppho5; and
(4) XS-30-2B (transformed by pYGA2269) having the promoter $P_{GAP}$.

Starting pre-culture was prepared by inoculating a platinum loopful of the yeast in a minimum nutrient medium (5 ml) containing 1% Casamino acids, uracil and adenine and shake-culturing at 28° C. for 20 hours. This starting preculture was inoculated in a YPD medium in an amount of two percent and subjected to stationary cultivation at 28° C. for 24 hours to obtain a final pre-culture. The final pre-culture was inoculated in YPS medium at five percent and subjected to stationary cultivation at 28° C. for the purpose of investigating ethanol production. The cultivation of yeast strain (3) on and after the final pre-culture was conducted in a low phosphate YPD or YPS medium respectively with a view to inducing Ppho5. The same experiment was conducted for three different starch concentrations (1, 2 and 5%). The results of ethanol production and yeast growth are shown in Tables 1 and 2.

TABLE 1

| No. | Yeast | Starch (%) | | Time (hrs) | | | | |
|---|---|---|---|---|---|---|---|---|
| | | | | 0 | 24 | 48 | 72 | 96 |
| 1 | XS-30-2B | 1 | GA (U/ml) | 0 | 0 | 0 | 0 | 0 |
| | | | EtOH (v/v %) | | 0.03 | 0.03 | 0.04 | 0.03 |
| 2 | [pYGA2149] | 2 | GA | 0 | 0 | 0 | 0 | 0 |
| | | | EtOH | | 0.03 | 0.02 | 0.03 | 0.05 |
| 3 | 2 | 5 | GA | 0 | 0 | 0 | 0 | 0 |
| | | | EtOH | | 0.03 | 0.03 | 0.04 | 0.03 |
| 4 | XS-30-2B | 1 | GA | 0.020 | 0.058 | 0.124 | 0.137 | 0.134 |
| | | | EtOH | | 0.12 | 0.19 | 0.44 | 0.29 |
| 5 | [pYGA2169] | 2 | GA | 0.020 | 0.069 | 0.339 | 0.399 | 0.429 |
| | | | EtOH | | 0.24 | 0.55 | 0.71 | 0.23 |
| 6 | 3 | 5 | GA | 0.020 | 0.031 | 0.488 | 0.763 | 0.833 |
| | | | EtOH | | 0.23 | 0.77 | (2.68) | 1.94 |
| 7 | XS-30-2B | 1 | GA | 0.030 | 0.041 | 0.091 | 0.089 | 0.116 |
| | | | EtOH | | 0.11 | 0.49 | 0.32 | |
| 8 | [pYGA2269] | 2 | GA | 0.030 | 0.067 | 0.181 | 0.174 | 0.214 |
| | | | EtOH | | 0.34 | 1.00 | 0.68 | |

TABLE 1-continued

| No. | Yeast | Starch (%) | | Time (hrs) | | | | |
|---|---|---|---|---|---|---|---|---|
| | | | | 0 | 24 | 48 | 72 | 96 |
| 9 | 4 | 5 | GA | 0.030 | 0.082 | 0.294 | 0.311 | 0.383 |
| | | | EtOH | | 0.33 | 1.92 | (2.12) | |
| 10 | XS-30-2B | 1 | GA | 0 | 0 | 0 | 0 | 0 |
| | | | EtOH | | 0.03 | 0.03 | 0.02 | |
| 11 | 1 | 2 | GA | 0 | 0 | 0 | 0 | 0 |
| | | | EtOH | | 0.03 | 0.04 | 0.04 | |
| 12 | | 5 | GA | 0 | 0 | 0 | 0 | 0 |
| | | | EtOH | | 0.03 | 0.03 | 0.03 | |

GA: glucoamylase
EtOH: ethanol

TABLE 2

| | Utilization for 2% starch at 48 hour | | |
|---|---|---|---|
| Yeast | GA (U/ml) | EtOH (v/v %) | Yield (%) |
| XS-30-2B [pYGA2169] 3 | 0.34 | 0.55 | 40.4 |
| XS-30-2B [pYGA2269] 4 | 0.18 | 1.00 | 73.5 |
| XS-30-2B 1 | 0 | 0.04 | 0 |

(h-ii)

Alcohol fermentation with low-temperature cooked starch

Ground corn (140 g) was added to 402 ml of water, and after adding 0.5 g of α-amylase preparation (Termamil) as a viscosity reducer and 160 ppm of potassium metabisulfite as a germicide, the mixture was held at 80°–82° C. for 5 minutes, and then rapidly cooled.

Figure 10:
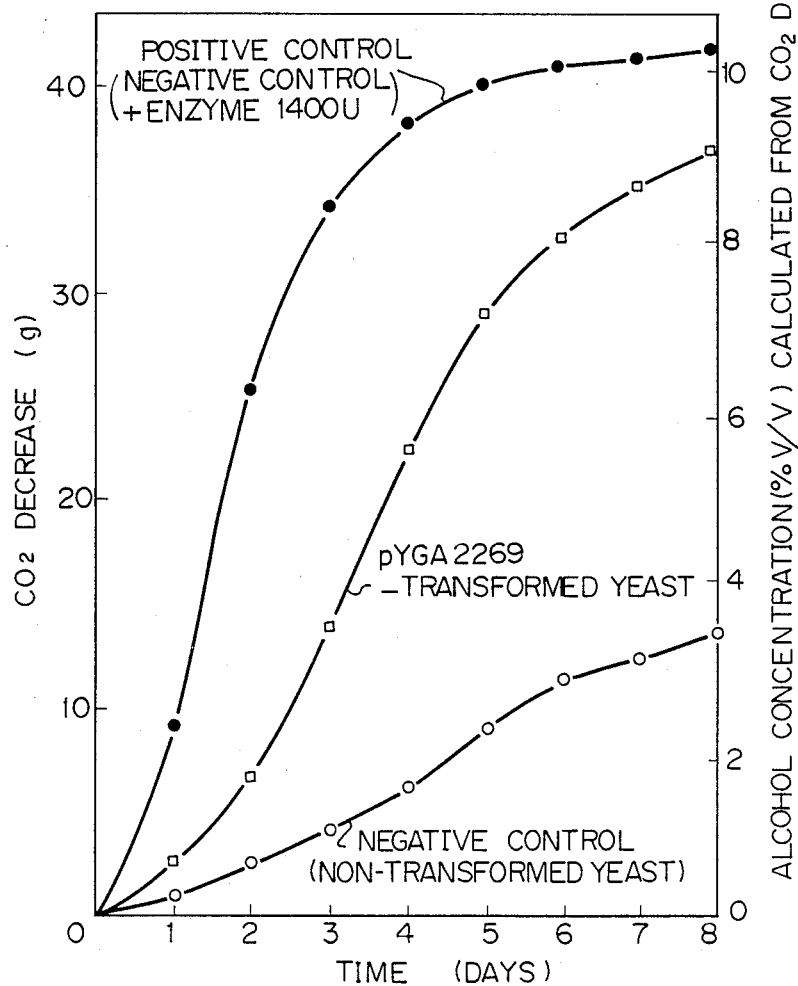
FIG. 10 is a graph showing the profile of alcohol production by one of the transformed yeasts prepared in Example 1.

Starting and final pre-cultures were prepared using the same strain as employed in (h-i) and the final pre-culture was added to the low-temperature cooked starch and the mixture was cultured at 28° C. under three different conditions, i.e., in the absence of any additional component, in the presence of Casamino acids, uracil and adenine, and in the presence of Casamino acids, uracil, adenine and 0.4% glucose. The progress of fermentation (as evaluated in terms of the decrease in $CO_2$) and alcohol production were investigated. A non-transformed yeast using the routine amount of Rhizopus glucoamylase was employed as a positive control. The results are shown in Tables 3 and 4 and in FIG. 10, from which one can see that the yeasts obtained in accordance with the present invention were capable of direct alcohol production from non-cooked or low-temperature cooked (LTC) starch without addition of a Rhizopus glucoamylase preparation.

TABLE 3

| | | | | | $CO_2$ Reduction (g) | | | | | |
|---|---|---|---|---|---|---|---|---|---|---|
| No. | Yeast | Casamino acids | Glucose | Enzyme* | 0 | 24 | 48 | 72 | 96 | 192 |
| 1 | XS-30-2B | | | | 0 | 0.33 | 3.05 | 6.62 | 11.4 | |
| 2 | [pYGA2149] | O | | | 0 | 0.51 | 3.85 | 6.00 | 7.15 | |
| 3 | ② | O | O | | 0 | 1.67 | 4.69 | 7.32 | 10.70 | |
| 4 | XS-30-2B | | | | 0 | 1.05 | 3.77 | 5.84 | 8.15 | |
| 5 | [pYGA2169] | O | | | 0 | 1.09 | 4.28 | 5.89 | 7.61 | |
| 6 | ③ | O | O | | 0 | 2.07 | 4.96 | 6.87 | 9.52 | |
| 7 | XS-30-2B | | | | 0 | 1.85 | 4.10 | 6.22 | 8.03 | |
| 8 | [pYGA2269] | O | | | 0 | 2.78 | 6.83 | 14.22 | 22.68 | 37.55 |
| 9 | ④ | O | O | | 0 | 3.89 | 8.18 | 13.75 | 19.17 | |
| 10 | XS-30-2B | | | | 0 | 0.65 | 2.38 | 2.97 | 4.04 | |
| 11 | | O | | | 0 | 1.01 | 2.67 | 4.22 | 6.45 | 14.36 |
| 12 | (control) | O | O | | 0 | 1.93 | 3.86 | 4.74 | 5.14 | |
| 13 | ① | O | | O | 0 | 9.25 | 25.43 | 34.14 | 38.38 | 42.27 |

Feed: 500 ml
*: Rhizopus glucoamylase

TABLE 4

| | | | | | Alcohol production (v/v %) | | | | | |
|---|---|---|---|---|---|---|---|---|---|---|
| No. | Yeast | Casamino acids | Glucose | Enzyme* | 0 | 24 | 48 | 72 | 96 | 192 |
| 1 | XS-30-2B | | | | 0 | 0.0789 | 0.730 | 1.584 | 2.727 | |
| 2 | [pYGA2149] | O | | | 0 | 0.122 | 0.921 | 1.435 | 1.711 | |
| 3 | ② | O | O | | 0 | 0.400 | 1.122 | 1.751 | 2.560 | |
| 4 | XS-30-2B | | | | 0 | 0.251 | 0.902 | 1.397 | 1.950 | |
| 5 | [pYGA2169] | O | | | 0 | 0.261 | 1.024 | 1.409 | 1.821 | |
| 6 | ③ | O | O | | 0 | 0.495 | 1.187 | 1.344 | 2.278 | |
| 7 | XS-30-2B | | | | 0 | 0.443 | 0.931 | 1.488 | 1.921 | |
| 8 | [pYGA2269] | O | | | 0 | 0.665 | 1.634 | 3.402 | 5.426 | 9.0 |
| 9 | ④ | O | O | | 0 | 0.931 | 1.957 | 3.289 | 4.586 | |
| 10 | XS-30-2B | | | | 0 | 0.156 | 0.569 | 0.711 | 0.967 | |
| 11 | | O | | | 0 | 0.242 | 0.639 | 1.009 | 1.543 | 3.4 |
| 12 | (control) | O | O | | 0 | 0.462 | 0.923 | 1.134 | 1.230 | |

TABLE 4-continued

| | | | | Alcohol production (v/v %) | | | | | |
|---|---|---|---|---|---|---|---|---|---|
| | | Casamino | | | | Time (hrs) | | | |
| No. | Yeast | acids | Glucose | Enzyme* | 0 | 24 | 48 | 72 | 96 | 192 |
| 13 | ① | O | | O | 0 | 2.213 | 6.084 | 8.167 | 9.182 | 10.1 |

Feed: 500 ml
*: Rhizopus glucoamylase

EXAMPLE 2

(a)

A 2.0 kb DNA fragment containing glucoamylase gene from pYGA2269 prepared in Example 1(e) was inserted into the HindIII site of a known vector YCp19, whereby pYGA195 was obtained (FIG. 6C). This plasmid, containing a centromere was present in yeast with a copy number of 1.

(b)

Expression of glucoamylase gene in yeast

The plasmids, pYGA2269 and pYGA195, were used to transform yeast strain XS-30-2B (MATα, Leu2, his3, trpl, ura3) and the transformed colonies were selected by the nutrient requirement for tryptophan as a marker. Transformation was conducted by the method of Ito et al (ibid) using LiCl. The selected transformed colonies were cultured overnight at 30° C. in 5 ml of a minimum nutrient medium (0.67% Yeast Nitrogen base, 2% glucose, 0.001% uracil, 0.0054% adenine, 0.0026% leucine and 0.0038% histidine). The culture solution was inoculated at one percent in 400 ml of the minimum nutrient medium in an Erlenmeyer flask (1,000 ml) and shake-cultured at 30° C.

Figure 11:
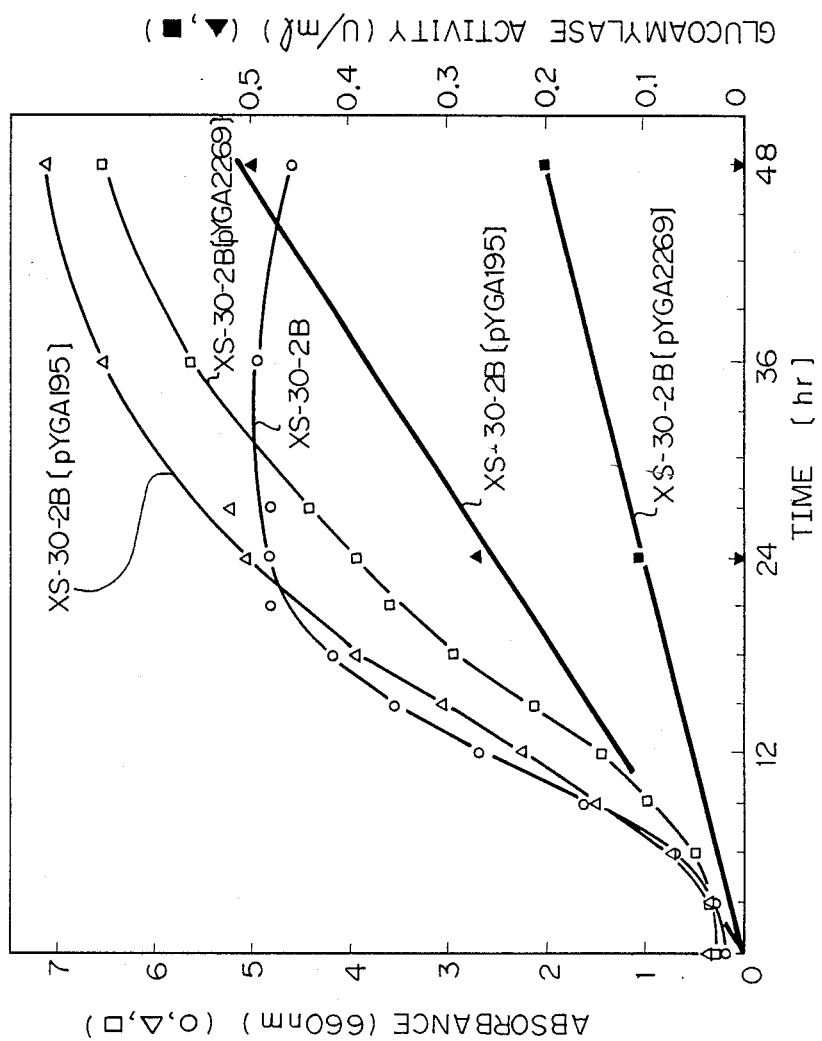
FIG. 11 is a graph showing the production of glucoamylase by the transformed yeasts obtained in Example 2.

Sampling was conducted at approximate intervals of 3 hours, and the absorbance at 660 nm and the glucoamylase activity values at 24 and 48 hours were determined, by measuring the amount of free glucose that was released by reaction at 37° C. of a mixture of the supernatant of the culture (50 μl) and 950 μl of a soluble starch solution (0.5% soluble starch in 20 mM acetate buffer, pH 4.5). The amount of glucose was determined by a glucostat of Fujisawa Pharmaceutical Co., Ltd. One unit (U) of glucoamylase activity corresponds to 1 μmole of glucose released in 1 minute. The yeasts transformed by pYGA2269 and pYGA195 produced glucoamylase activities in amounts of 0.2 U/ml and 0.5 U/ml, respectively, at 48 hours (see FIG. 11). This enzyme can be secreted in an adequate amount even from a plasmid with a copy number of 1 by expressing it in the presence of a strong promoter such as GAPDH promoter.

(c)

Purification of the enzyme obtained by the recombinant DNA technology

S. cerevisiae XS-30-2B transformed by pYGA2269 was cultured for 3 days at 30° C. in a medium containing 0.67% Yeast Nitrogen base, 2% Casamino acids, 2% glucose, 0.001% uracil, 0.0054% adenine, 0.0026% leucine and 0.0038% histidine. The supernatant of the culture was concentrated about 20-folds by an Amicon concentrator, dialyzed against an acetate buffer (20 mM $CH_3l$ $COONa$, $pH$ 4.6), and adsorbed on an SP-Sephadex C-50 column equilibrated with the same buffer. A linear gradient from 0 to 200 mmol was applied to the column, whereby the active fractions eluted were recovered, dialyzed against water, freeze-dried and stored for the following experiments.

(d)

Properties of enzymes

The amino acid composition of the glucoamylase produced by the recombinant yeast was in good agreement with the Gluc 1 having the highest molecular weight of the three glucoamylase molecules produced by the Rhizopus; the N-terminal sequence and isoelectric point of the glucoamylase were also the same as those of the Rhizopus-produced glucoamylase. The apparent molecular weight of the glucoamylase as determined by SDS-polyacrylamide electrophoresis was slightly higher than that of Gluc 1. The molecular weight of the glucomaylase was decreased by digestion with endoglycosidase H capable of cutting a certain sugar chain attached to the asparagine residue. However, the Rhizopus-produced glucoamylase is not sensitive to the action of endoglycosidase H. The difference between the two glucoamylase molecules with respect to the molecular weight would be ascribable to the differences in the amount and mode of sugar chain attachment.

No difference was observed with respect to pH dependency, heat stability or other parameters such as Vmax and Km for soluble starch. The Rhizopus-produced glucoamylase had an r/s value (r: activity on raw starch, s: activity on gelatinized soluble starch) of 0.47 while the value for the recombinant yeast produced glucoamylase was 0.56. It is therefore concluded that as far as the ability to decompose raw starch is concerned, a better glucoamylase preparation can be produced from the recombinant yeast, rather than from the Rhizopus.

(e)

Adsorption site on starch

The Rhizopus-produced glucoamylase contains three molecules having different molecular weights, Gluc 1, 2 and 3, the last two of which would be the product of limited proteolysis of the N-terminal amino acid sequence of Gluc 1.

The behavior of these three molecules in adsorption to starch was investigated. A sample of enzyme solution was mixed with an equal volume of raw starch and, after leaving the mixture to stand in iced water for 30 minutes, it was subjected to centrifugation. The supernatant was recovered as a fraction of the enzyme which was not adsorbed on the starch while the precipitate was recovered as a fraction which was adsorbed on starch. Both fractions were analyzed by SDS-PAGE; Gluc 1 and the recombinant yeast produced glucoamylase were found in the precipitate whereas Gluc 2 and 3 were found in the supernatant. The mixture of Gluc 2 and 3 had an r/s value of 0.23, indicating that the Rhizopus glucomaylase lost its ability to be adsorbed onto raw starch by becoming deficient of the N-terminal sequence. It is therefore concluded that the N-terminal portion has a site which is adsorbed on raw starch. The Rhizopus glucoamylase was capable of hydrolysing gelatinized soluble starch as effectively as the glucoamylase of the full length even if it lost the N-terminal portion. When a mixture of glucoamylase solution with gelatinized soluble starch was subjected to column chromatography on Ultrogel AcA 44, both Gluc 1 and the recombinant yeast produced glucomaylase were eluted in the void volumes in the column together with the starch, but neither Gluc 2 nor 3 was adsorbed on the starch and they were eluted in the corresponding elution volumes. This provided a basis for the conclusion that Gluc 1 and the recombinant yeast produced glucoamylase are capable of adsorption not only on raw starch but also on gelatinized starch.

What is claimed is:

1. The *Rhizopus oryzae* glucoamylase structural gene consisting of the following nucleotide sequence:

GCA AGC ATT CCT AGT AGT GCT TCT GTC CAG (II)

240
CTT GAT TCA TAC AAT TAC GAT GGC TCT ACT

TTT TCA GGA AAA ATT TAT GTC AAG AAC ATT

300
GCT TAC TCC AAG AAG GTT ACT GTA ATT TAC

GCC GAT GGC TCT GAC AAC TGG AAT AAT AAT

360
GGA AAC ACC ATT GCT GCT TCT TAC TCT GCT

CCT ATT TCT GGA TCA AAT TAC GAA TAC TGG

420
ACA TTC TCT GCC TCC ATT AAT GGT ATC AAG

GAG TTC TAC ATT AAG TAT GAG GTC AGT GGA

480
AAA ACA TAC TAT GAT AAC AAC AAT TCT GCC

AAT TAC CAA GTA TCT ACA TCC AAG CCT ACT

540
ACT ACT ACT GCT ACT GCT ACT ACT ACT ACC

GCT CCT TCC ACT TCA ACC ACG ACT CCC CCC

600
TCA AGC TCT GAG CCA GCT ACT TTC CCA ACT

GGT AAC TCT ACA ATC TCC TCA TGG ATT AAG

660
AAG CAA GAA GGT ATC AGC CGC TTT GCT ATG

CTT CGA AAC ATC AAT CCT CCT GGA AGC GCT

720
ACC GGT TTC ATT GCT GCC TCA CTC TCT ACC

GCT GGT CCC GAT TAC TAC TAT GCT TGG ACT

780
CGT GAT GCT GCA TTA ACC TCC AAT GTA ATT

GTT TAC GAA TAC AAC ACT ACT TTG TCC GGT

840
AAT AAG ACT ATC CTC AAC GTC CTC AAG GAC

TAT GTT ACA TTC TCA GTC AAG ACC CAA TCA

900
ACT TCT ACC GTC TGT AAC TGC CTT GGT GAG

CCT AAG TTC AAT CCT GAT GGT TCT GGC TAT

960
ACT GGT GCT TGG GGA AGA CCT CAA AAT GAT

GGA CCT GCT GAA CGT GCT ACT ACC TTC ATT

1020
TTG TTT GCT GAC AGT TAT CTT ACT CAA ACA

AAG GAT GCT TCC TAT GTC ACT GGT ACA CTC

1080
AAG CCT GCT ATC TTC AAG GAC TTG GAC TAT

GTC GTC AAT GTC TGG TCT AAT GGC TGT TTC

1140
GAT TTA TGG GAA GAA GTC AAC GGT GTT CAC

TTC TAT ACT TTA ATG GTT ATG CGT AAG GGT

1200
TTG CTT CTT GGT GCA GAT TTC GCT AAA CGT

AAC GGT GAC TCT ACT CGT GCA TCT ACC TAT

1260
ACG AGC ACT GCA TCC ACT ATT GCA AAC AAG

ATC TCT AGC TTC TGG GTT TCT TCT AAT AAC

1320
TGG ATT CAA GTC AGT CAA AGC GTT ACT GGT

GGT GTC AGT AAA AAG GGT TTG GAT GTC TCC

1380
ACA TTG TTG GCT GCT AAC CTT GGT AGT GTT

GAT GAT GGA TTC TTC ACT CCT GGC TCT GAA

1440
AAG ATC CTT GCC ACT GCT GTT GCT GTT GAA

GAC TCC TTC GCT TCC TTG TAT CCT ATC AAC

1500
AAA AAC CTT CCA TCT TAC CTT GGT AAC TCT

ATT GGT AGA TAT CCT GAA GAC ACT TAC AAT

1560
GGT AAC GGA AAC TCT CAA GGA AAC TCT TGG

TTC TTG GCT GTA ACT GGT TAC GCT GAG CTC

1620
TAT TAC CGT GCC ATC AAG GAA TGG ATC GGC

AAC GGT GGT GTC ACT GTC AGC AGC ATA AGT

1680
TTA CCC TTC TTC AAG AAG TTT GAT TCA TCT

GCT ACA TCT GGA AAG AAG TAC ACT GTT GGT

1740
ACC TCC GAC TTT AAC AAC CTT GCT CAA AAT

ATT GCA CTC GCT GCT GAC CGT TTC TTG TCC

1800
ACT GTC CAG CTC CAT GCT CAC AAC AAT GGA

TCT CTT GCT GAA GAG TTT GAC CGC ACC ACT

1860
GGT TTA TCC ACC GGT GCT AGA GAC TTG ACC

TGG TCT CAC GCT TCT TTA ATC ACC GCT TCT

-continued
1920
TAC GCT AAG GCT GGT GCA CCT GCC GCT

2. The *Rhizopus oryzae* glucoamylase structural gene wherein the gene encodes the following amino acid sequence:

(I)

```
                30                          40
Ala Ser Ile Pro Ser Ser Ala Ser Val Gln Leu Asp Ser Tyr Asn Tyr Asp Gly Ser Thr Phe Ser Gly Lys 50                          60                          70
Ile Tyr Val Lys Asn Ile Ala Tyr Ser Lys Lys Val Thr Val Ile Tyr Ala Asn Gly Ser Asp Asn Trp Asn 80                          90
Asn Asn Gly Asn Thr Ile Ala Ala Ser Tyr Ser Ala Pro Ile Ser Gly Ser Asn Tyr Glu Tyr Trp Thr Phe 100                         110                         120
Ser Ala Ser Ile Asn Gly Ile Lys Glu Phe Tyr Ile Lys Tyr Glu Val Ser Gly Lys Thr Tyr Tyr Asp Asn 130                         140
Asn Asn Ser Ala Asn Tyr Gln Val Ser Thr Ser Lys Pro Thr Thr Thr Thr Ala Thr Ala Thr Thr Thr Thr 150                         160
Ala Pro Ser Thr Ser Thr Thr Thr Pro Pro Ser Ser Ser Glu Pro Ala Thr Phe Pro Thr Gly Asn Ser Thr 170                         180                         190
Ile Ser Ser Trp Ile Lys Lys Gln Glu Gly Ile Ser Arg Phe Ala Met Leu Arg Asn Ile Asn Pro Pro Gly 200                         210
Ser Ala Thr Gly Phe Ile Ala Ala Ser Leu Ser Thr Ala Gly Pro Asp Tyr Tyr Tyr Ala Trp Thr Arg Asp 220                         230                         240
Ala Ala Leu Thr Ser Asn Val Ile Val Tyr Glu Tyr Asn Thr Thr Leu Ser Gly Asn Lys Thr Ile Leu Asn 250                         260
Val Leu Lys Asp Tyr Val Thr Phe Ser Val Lys Thr Gln Ser Thr Ser Thr Val Cys Asn Cys Leu Gly Glu 270                         280
Pro Lys Phe Asn Pro Asp Gly Ser Gly Tyr Thr Gly Ala Trp Gly Arg Pro Gln Asn Asp Gly Pro Ala Glu 290                         300                         310
Arg Ala Thr Thr Phe Ile Leu Phe Ala Asp Ser Tyr Leu Thr Gln Thr Lys Asp Ala Ser Tyr Val Thr Gly 320                         330
Thr Leu Lys Pro Ala Ile Phe Lys Asp Leu Asp Tyr Val Val Asn Val Trp Ser Asn Gly Cys Phe Asp Leu 340                         350                         360
Trp Glu Glu Val Asn Gly Val His Phe Tyr Thr Leu Met Val Met Arg Lys Gly Leu Leu Leu Gly Ala Asp 370                         380
Phe Ala Lys Arg Asn Gly Asp Ser Thr Arg Ala Ser Thr Tyr Ser Ser Thr Ala Ser Thr Ile Ala Asn Lys 390                         400
Ile Ser Ser Phe Trp Val Ser Ser Asn Asn Trp Ile Gln Val Ser Gln Ser Val Thr Gly Gly Val Ser Lys 410                         420                         430
Lys Gly Leu Asp Val Ser Thr Leu Leu Ala Ala Asn Leu Gly Ser Val Asp Asp Gly Phe Phe Thr Pro Gly 440                         450
Ser Glu Lys Ile Leu Ala Thr Ala Val Ala Val Glu Asp Ser Phe Ala Ser Leu Tyr Pro Ile Asn Lys Asn 460                         470                         480
Leu Pro Ser Tyr Leu Gly Asn Ser Ile Gly Arg Tyr Pro Glu Asp Thr Tyr Asn Gly Asn Gly Asn Ser Gln 490                         500
Gly Asn Ser Trp Phe Leu Ala Val Thr Gly Tyr Ala Glu Leu Tyr Tyr Arg Ala Ile Lys Glu Trp Ile Gly 510                         520
Asn Gly Gly Val Thr Val Ser Ser Ile Ser Leu Pro Phe Phe Lys Lys Phe Asp Ser Ser Ala Thr Ser Gly 530                         540                         550
Lys Lys Tyr Thr Val Gly Thr Ser Asp Phe Asn Asn Leu Ala Gln Asn Ile Ala Leu Ala Ala Asp Arg Phe 560                         570
Leu Ser Thr Val Gln Leu His Ala His Asn Asn Gly Ser Leu Ala Glu Glu Phe Asp Arg Thr Thr GLy Leu 580                         590                         600
Ser Thr Gly Ala Arg Asp Leu Thr Trp Ser His Ala Ser Leu Ile Thr Ala Ser Tyr Ala Lys Ala Gly Ala

Pro Ala Ala
```

3. The recombinant DNA of claim 1, operatively-linked to the *Rhizopus oryzae* glucoamylase gene signal sequence consisting of the following nucleotide sequence:

| | | | | | | | | | |
|---|---|---|---|---|---|---|---|---|---|
| ATG | CAA | CTG | TTC | AAT | TTG | CCA | TTG | AAA | GTT |
| TCA | TTC | TTT | CTC | GTC | CTC | TCT | TAC | TTT | TCT |
| TTG | CTC | GTT | TCT | GCT. | | | | | |

4. The recombinant DNA of claim 2 which encodes the following amino acid sequence:

(III)

```
                          10                                          20
MET GLN LEU PHE ASN LEU PRO LEU LYS VAL SER PHE PHE LEU VAL LEU SER TYR PHE SER LEU LEU 30                            40
VAL SER ALA Ala Ser Ile Pro Ser Ser Ala Ser Val Gln Leu Asp Ser Tyr Asn Tyr Asp Gly Ser Thr Phe Ser Gly 50                       60                       70
Lys Ile Tyr Val Lys Asn Ile Ala Tyr Ser Lys Lys Val Thr Val Ile Tyr Ala Asn Gly Ser Asp Asn Trp 80                        90
Asn Asn Asn Gly Asn Thr Ile Ala Ala Ser Tyr Ser Ala Pro Ile Ser Gly Ser Asn Tyr Glu Tyr Trp Thr 100                      110                        120
Phe Ser Ala Ser Ile Asn Gly Ile Lys Glu Phe Tyr Ile Lys Tyr Glu Val Ser Gly Lys Thr Tyr Tyr Asp 130                           140
Asn Asn Asn Ser Ala Asn Tyr Gln Val Ser Thr Ser Lys Pro Thr Thr Thr Thr Ala Thr Ala Thr Thr Thr 150                              160
Thr Ala Pro Ser Thr Ser Thr Thr Thr Pro Pro Ser Ser Ser Glu Pro Ala Thr Phe Pro Thr Gly Asn Ser 170                            180                         190
Thr Ile Ser Ser Trp Ile Lys Lys Gln Glu Gly Ile Ser Arg Phe Ala Met Leu Arg Asn Ile Asn Pro Pro 200                           210
Gly Ser Ala Thr Gly Phe Ile Ala Ala Ser Leu Ser Thr Ala Gly Pro Asp Tyr Tyr Ala Trp Thr Arg 220                            230                         240
Asp Ala Ala Leu Thr Ser Asn Val Ile Val Tyr Glu Tyr Asn Thr Thr Leu Ser Gly Asn Lys Thr Ile Leu 250                         260
Asn Val Leu Lys Asp Tyr Val Thr Phe Ser Val Lys Thr Gln Ser Thr Ser Thr Val Cys Asn Cys Leu Gly 270                          280
Glu Pro Lys Phe Asn Pro Asp Gly Ser Gly Tyr Thr Gly Ala Trp Gly Arg Pro Gln Asn Asp Gly Pro Ala 290                        300                           310
Glu Arg Ala Thr Thr Phe Ile Leu Phe Ala Asp Ser Tyr Leu Thr Gln Thr Lys Asp Ala Ser Tyr Val Thr 320                         330
Gly Thr Leu Lys Pro Ala Ile Phe Lys Asp Leu Asp Tyr Val Val Asn Val Trp Ser Asn Gly Cys Phe Asp 340                          350                              360
Leu Trp Glu Glu Val Asn Gly Val His Phe Tyr Thr Leu Met Val Met Arg Lys Gly Leu Leu Leu Gly Ala 370                            380
Asp Phe Ala Lys Arg Asn Gly Asp Ser Thr Arg Ala Ser Thr Tyr Ser Ser Thr Ala Ser Thr Ile Ala Asn 390                          400
Lys Ile Ser Ser Phe Trp Val Ser Ser Asn Asn Trp Ile Gln Val Ser Gln Ser Val Thr Gly Gly Val Ser 410                          420                           430
Lys Lys Gly Leu Asp Val Ser Thr Leu Leu Ala Ala Asn Leu Gly Ser Val Asp Asp Gly Phe Phe Thr Pro 440                         450
Gly Ser Glu Lys Ile Leu Ala Thr Ala Val Ala Val Glu Asp Ser Phe Ala Ser Leu Tyr Pro Ile Asn Lys 460                            470                              480
Asn Leu Pro Ser Tyr Leu Gly Asn Ser Ile Gly Arg Tyr Pro Glu Asp Thr Tyr Asn Gly Asn Gly Asn Ser 490                              500
Gln Gly Asn Ser Trp Phe Leu Ala Val Thr Gly Tyr Ala Glu Leu Tyr Tyr Arg Ala Ile Lys Glu Trp Ile 510                             520
Gly Asn Gly Gly Val Thr Val Ser Ser Ile Ser Leu Pro Phe Phe Lys Lys Phe Asp Ser Ser Ala Thr Ser 530                             540                              550
Gly Lys Lys Tyr Thr Val Gly Thr Ser Asp Phe Asn Asn Leu Ala Gln Asn Ile Ala Leu Ala Ala Asp Arg 560                             570
Phe Leu Ser Thr Val Gln Leu His Ala His Asn Asn Gly Ser Leu Ala Glu Glu Phe Asp Arg Thr Thr Gly
```

```
                580                         590                              600
Leu Ser Thr Gly Ala Arg Asp Leu Thr Trp Ser His Ala Ser Leu Ile Thr Ala Ser Tyr Ala Lys Ala Gly

Ala Pro Ala Ala
```

5. A recombinant vector comprising the glucoamylase structural gene of claim 1.

6. A recombinant vector comprising the glucoamylase gene of claim 3.

7. A plasmid selected from the group consisting of pCGA449, pCGA469, pYGA2249, pYGA2149, pYGA2269 and pYGA195.

8. A microorganism transformed by the vector of claim 5.

9. A microorganism transformed by the vector of claim 6.

10. A microorganism transformed by plasmid pCGA449, pCGA469, pYGA2169, pYGA2149, pYGA2269 or pYGA195.

11. A process for producing glucoamylase of the genus *Rhizopus oryzae* capable of efficient hydrolysis of raw starch, said process comprising the steps of:

(a) transforming *Saccharomyces cerevisae* yeast cells with a recombinant expression vector which comprises the glucoamylase structural gene of claim 1;

(b) cultivating said yeast cells in a liquid medium capable of inducing the expression of the glucoamylase structural gene; and, (c) recovering said glucoamylase from the medium or cells.

12. A process according to claim 11, wherein said glucoamylase structural gene is operatively linked to the *Rhizopus oryzae* glucoamylase signal peptide-encoding sequence, wherein cultivation is carried out under conditions which enable the glucoamylase to be secreted from said yeast cells into the culture medium from which medium the glucoamylase is then recovered.

* * * * *